United States Patent
Tseng et al.

(10) Patent No.: US 9,175,066 B2
(45) Date of Patent: Nov. 3, 2015

(54) COMPOSITIONS CONTAINING HC-HA COMPLEX AND METHODS OF USE THEREOF

(75) Inventors: Scheffer Tseng, Pinecrest, FL (US); Hua He, Miami, FL (US)

(73) Assignee: TISSUETECH, INC., Miami, FL (US)

( * ) Notice: Subject to any disclaimer, the term of this patent is extended or adjusted under 35 U.S.C. 154(b) by 721 days.

(21) Appl. No.: 13/262,725

(22) PCT Filed: Apr. 26, 2010

(86) PCT No.: PCT/US2010/032452
§ 371 (c)(1),
(2), (4) Date: Dec. 16, 2011

(87) PCT Pub. No.: WO2010/124296
PCT Pub. Date: Oct. 28, 2010

(65) Prior Publication Data
US 2012/0083445 A1    Apr. 5, 2012

Related U.S. Application Data

(60) Provisional application No. 61/172,621, filed on Apr. 24, 2009, provisional application No. 61/267,776, filed on Dec. 8, 2009.

(51) Int. Cl.
*C07K 14/805* (2006.01)
*A61K 38/00* (2006.01)
*A61K 38/05* (2006.01)
*C07K 14/78* (2006.01)
*A61K 47/48* (2006.01)

(52) U.S. Cl.
CPC .............. *C07K 14/78* (2013.01); *A61K 47/481* (2013.01); *A61K 38/00* (2013.01)

(58) Field of Classification Search
CPC ........ C07K 14/805; A61K 38/00; A61K 38/05
See application file for complete search history.

(56) References Cited

U.S. PATENT DOCUMENTS

| | | | |
|---|---|---|---|
| 3,598,122 A | 8/1971 | Zaffaroni |
| 3,598,123 A | 8/1971 | Zaffaroni |
| 3,710,795 A | 1/1973 | Higuchi et al. |
| 3,731,683 A | 5/1973 | Zaffaroni |
| 3,742,951 A | 7/1973 | Zaffarini |
| 3,814,097 A | 6/1974 | Ganderton et al. |
| 3,921,636 A | 11/1975 | Zaffaroni |
| 3,972,995 A | 8/1976 | Tsuk et al. |
| 3,993,072 A | 11/1976 | Zaffaroni |
| 3,993,073 A | 11/1976 | Zaffaroni |
| 3,996,934 A | 12/1976 | Zaffaroni |
| 4,031,894 A | 6/1977 | Urquhart et al. |
| 4,060,084 A | 11/1977 | Chandrasekaran et al. |
| 4,069,307 A | 1/1978 | Higuchi et al. |
| 4,077,407 A | 3/1978 | Theeuwes et al. |
| 4,201,211 A | 5/1980 | Chandrasekaran et al. |
| 4,230,105 A | 10/1980 | Harwood |
| 4,292,299 A | 9/1981 | Suzuki et al. |
| 4,292,303 A | 9/1981 | Keith et al. |
| 4,305,502 A | 12/1981 | Gregory |
| 4,327,725 A | 5/1982 | Cortese et al. |
| 4,476,116 A | 10/1984 | Anik |
| 4,624,848 A | 11/1986 | Lee |
| 4,871,549 A | 10/1989 | Ueda et al. |
| 4,968,509 A | 11/1990 | Radebaugh et al. |
| 5,002,071 A | 3/1991 | Harrell |
| 5,011,692 A | 4/1991 | Fujioka et al. |
| 5,017,381 A | 5/1991 | Mariyama et al. |
| 5,033,252 A | 7/1991 | Carter |
| 5,052,558 A | 10/1991 | Carter |
| 5,093,487 A | 3/1992 | Brown et al. |
| 5,116,817 A | 5/1992 | Anik |
| 5,192,744 A | 3/1993 | Bouck et al. |
| 5,229,135 A | 7/1993 | Philippon et al. |
| 5,260,068 A | 11/1993 | Chen |
| 5,260,069 A | 11/1993 | Chen |
| 5,323,907 A | 6/1994 | Kalvelage |
| 5,336,168 A | 8/1994 | Sibalis |
| 5,437,287 A | 8/1995 | Phillips et al. |
| 5,456,923 A | 10/1995 | Nakamichi et al. |
| 5,461,140 A | 10/1995 | Heller et al. |
| 5,508,040 A | 4/1996 | Chen |
| 5,516,527 A | 5/1996 | Curatolo |
| 5,567,441 A | 10/1996 | Chen |
| 5,622,721 A | 4/1997 | Dansereau et al. |
| 5,665,378 A | 9/1997 | Davis et al. |
| 5,686,105 A | 11/1997 | Kelm et al. |
| 5,700,410 A | 12/1997 | Nakamichi et al. |
| 5,837,280 A | 11/1998 | Kenealy et al. |
| 5,837,284 A | 11/1998 | Mehta et al. |

(Continued)

FOREIGN PATENT DOCUMENTS

JP    H01256967 A    10/1989
JP    2002515899 A    5/2002

(Continued)

OTHER PUBLICATIONS

Colon et al. J. Biol. Chem. 2009, 284:2320-2331.*

(Continued)

*Primary Examiner* — Karlheinz R Skowronek
*Assistant Examiner* — Li Lee
(74) *Attorney, Agent, or Firm* — Wilson Sonsini Goodrich Rosati

(57) ABSTRACT

Disclosed herein, in certain embodiments, is an HC•HA complex comprising hyaluronan and a heavy chain of IαI, wherein the transfer of the heavy chain of IαI is catalyzed by TSG-6. Further disclosed herein, in certain embodiments, is an HC•HA complex comprising hyaluronan and a heavy chain of IαI, wherein the transfer of the heavy chain of IαI is catalyzed by the TSG-6 like protein. Additionally, disclosed herein are methods of manufacturing said complex and methods of use thereof.

7 Claims, 14 Drawing Sheets

(56) References Cited

U.S. PATENT DOCUMENTS

| | | | |
|---|---|---|---|
| 5,840,329 | A | 11/1998 | Bai |
| 5,869,090 | A | 2/1999 | Rosenbaum |
| 5,932,545 | A | 8/1999 | Henkin et al. |
| 5,977,175 | A | 11/1999 | Lin |
| 6,152,142 | A | 11/2000 | Tseng |
| 6,326,019 | B1 | 12/2001 | Tseng et al. |
| 6,391,452 | B1 | 5/2002 | Antonsen et al. |
| 6,465,014 | B1 | 10/2002 | Moroni et al. |
| 6,923,983 | B2 | 8/2005 | Morgan et al. |
| 6,929,801 | B2 | 8/2005 | Klose et al. |
| 6,932,983 | B1 | 8/2005 | Straub et al. |
| 6,946,144 | B1 | 9/2005 | Jordan |
| 8,153,162 | B2 | 4/2012 | Tseng |
| 8,182,840 | B2 | 5/2012 | Tseng |
| 8,182,841 | B2 | 5/2012 | Tseng |
| 8,187,639 | B2 | 5/2012 | Tseng |
| 8,420,126 | B2 | 4/2013 | Tseng et al. |
| 8,440,235 | B2 | 5/2013 | Tseng et al. |
| 8,455,009 | B2 | 6/2013 | Tseng et al. |
| 8,460,714 | B2 | 6/2013 | Tseng et al. |
| 2001/0041684 | A1 | 11/2001 | Lazdey |
| 2004/0057938 | A1 | 3/2004 | Ghinelli |
| 2004/0126323 | A1 | 7/2004 | Shevchuk et al. |
| 2004/0181240 | A1 | 9/2004 | Tseng et al. |
| 2007/0071740 | A1* | 3/2007 | Tseng et al. ............ 424/94.1 |
| 2007/0071828 | A1 | 3/2007 | Tseng et al. |
| 2007/0231401 | A1 | 10/2007 | Tseng et al. |
| 2008/0102135 | A1 | 5/2008 | Ollivier |
| 2008/0193554 | A1 | 8/2008 | Dua et al. |
| 2008/0299087 | A1 | 12/2008 | Tseng et al. |
| 2009/0226499 | A1 | 9/2009 | Wisniewski et al. |
| 2012/0207848 | A1 | 8/2012 | Tseng |
| 2012/0207849 | A1 | 8/2012 | Tseng |
| 2012/0269880 | A1 | 10/2012 | Tseng et al. |
| 2012/0328690 | A1 | 12/2012 | Tseng et al. |
| 2013/0195992 | A1 | 8/2013 | Tseng et al. |
| 2013/0195993 | A1 | 8/2013 | Tseng et al. |
| 2013/0195994 | A1 | 8/2013 | Tseng et al. |
| 2013/0280344 | A1 | 10/2013 | Tseng et al. |

FOREIGN PATENT DOCUMENTS

| | | |
|---|---|---|
| KR | 2001-098716 A | 11/2001 |
| WO | WO-98-37903 | 9/1998 |
| WO | WO-03-077794 A2 | 9/2003 |
| WO | WO-2004-026244 | 4/2004 |
| WO | WO-2004-060388 | 7/2004 |
| WO | WO2007-038686 | 4/2005 |
| WO | WO-2005-060988 A1 | 7/2005 |
| WO | WO-2006-094247 A2 | 9/2006 |
| WO | WO2012/149486 | 1/2012 |
| WO | WO2014/011813 | 1/2014 |

OTHER PUBLICATIONS

Jadin et al. J Histochem Cytochem. Sep. 2014;62(9):672-83. doi: 10.1369/0022155414540176. Epub Jun. 2, 2014.*

Bae et al., "Characterization of the Promoter Region of the Human Transforming Growth Factor-β Type II Receptor Gene," *J. Biol. Chem.* 1995, 270(49):29460-29468.

Bhutto et al., "Localization of Collagen XVIII and the Endostatin Portion of Collagen XVIII in Ages Human Control Eyes and Eyes with Age-Related Macular Degeneration, " *Invest. Ophthalmol. Vis. Sci.* 2004, 45(5):1544-1552.

Border, W.A. and Ruoslahti, E., "Transforming Growth Factor-β in Disease: The Dark Side of Tissue Repair," *J. Clin. Invest.* 1992, 90:1-7.

Chen et al., " Recombinant Adenovirus Coexpressing Covalent Peptide/MHC Class II Complex and B7-1: In Vitro and In Vivo Activation of Myelin Basic Protein-Specific T Cells," *J. Immunol.* 2001, 167:1297-1305.

Chen et al., "Functions of hyaluronan in wound repair," *Wound Rep. Reg.* 1999, 7:79-89.

Day et al., "Hyaluronan cross-linking: a protective mechanism in inflammation?" Trends in Immunology 2005, 26(12):637-643.

Derynk, R. and Feng, X., "TGF-β receptor signaling," *Biochem. Biophys. Acta.* 1997, 1333:F105-F150.

Foutunato et al., "The effect of transforming growth factor and interleukin-10 on interleukin-8 release by human amniochorion may regulate histologic chorioamnionitis," *Am. J. Obstet. Gynecol.* 1998, 179:794-799.

Foutunato et al., "Interleukin-10 and transforming growth factor-β inhibit amniochorion tumor necrosis factor-α production by contrasting mechanisms of action: Therapeutic implications in prematurity," *Am. J. Obstet. Gynecol.* 1997, 177:803-809.

Foutunato et al., "Interleukin-10 inhibition of interleukin-6 in human amniochorionic membrane: Transcriptional regulation," *Am. J. Obstet. Gynecol.* 1996,175:1057-1065.

Fries et al., "Intera-a-inhibitor, hyaluronan and inflammation," *Acta Biochim. Polonica* 2003, 50(3):735-742.

Gabbiani, G., "The myofibroblast in wound healing and fibrocontractive diseases," *J. Pathol.* 2003, 200:500-503.

Grande, J.P., "Role of Transforming Growth Factor-β in Tissue Injury and Repair," *Proc. Soc. Exp. Biol. Med.* 1997, 214:27-40.

Guo, Jian-Hwa. "Carbopol® Ploymers for Pharmaceutical Druge Delivery Applications." *Drug Delivery Technology* 2003 vol. 3(6):1-4.

Hales et al., "TGF-β-1 induces lens cells to accumulate α-smooth muscle actin, a marker for subcapsular cataracts," Curr. Eye Res. 1994, 13:885-890.

Hanada et al., "Regulation of cytokine signaling and inflammation," Cytokine & Growth Factor Reviews 2002, 13(4-5):413-421.

Hao et al., "Identification of Antiangiogenic and Antiinflammatory Proteins in Human Amniotic Membrane," *Cornea* 2000, 19(3):348-352.

He et al., "A simplified system for generating recombinant adenoviruses," *PNAS USA* 1998, 95:2509-2514.

He et al., "Biochemical Characterization and Function of Complexes Formed by Hyaluronan and the Heavy Chains of Inter-a-inhibitor (HC-HA) Purified from Extracts of Human Amniotic Membrane," *J. Biol. Chem.* 2009, 284(30):20136-20146.

Heiligenhaus et al., "Improvement of HSV-1 Necrotizing Keratitis with Amniotic Membrane Transplantation," *Invest. Ophthalmol. Vis. Sci.* 2001, 42:1969-1974.

Howes et al., "Receptor for Advanced Glycation End Products and Age-Related Macular Degeneration," *Invest. Ophthal. Vis. Sci.* 2004, 45(10):3713-3720.

Jester et al., "Corneal Stromal Wound Healing in Refractive Surgery: the Role of Myofibroblasts," *Prog. Retin. Eye Res.* 1999, 18(3):311-356.

Jester et al., "Induction of α-Smooth Muscle Actin Expression and Myofibroblast Transformation in Cultured Cornea Keratocytes," *Cornea* 1996, 15:505-516.

Keelan et al., "Activin A Exerts both Pro- and -Anti-inflammatory Effectson Human Term Gestational Tissues," *Placenta* 2000, 31:38-43.

Kopp et al., "Abrogation of Transforming Growth Factor-beta Signaling by SMAD7 Inhibits Collagen Gel Contraction of Human Dermal Fibroblasts," *J. Biol. Chem.* 2005, 280(22):21570-21576.

Lawrence, D.A., "Transforming Growth Factor-β: a general review," *Eur. Cytokine Netw.* 1996, 7:363-374.

Lee, S.B. et al., "Suppression of TGFβ signaling in both normal conjuctival fibroblasts and pterygial body fibroblasts by amniotic membrane," *Curr. Eye Res.* 2000, 20(4):325-334.

Lee, S. and Tseng, S., "Amniotic Membrane Transplantation for Persistent Epithelial Defects with Ulceration," *Am. J. Ophthalmol.* 1997, 123:303-312.

Lee, H.G. and Cowman, M.K., "An Agarose Gel Electrophoretic Method for Analysis of Hyaluronan Molecular Weight Distribution," *Anal. Biochem.* 1994, 219:278-287.

Liberman et al., Pharmaceutical Dosage Forms, 1990, 2 Ed. vol. 1, pp. 209-214.

Liu et al., "Biocompatibility and stability of disulfide-corsslinked hyaluronan films," *Biomaterials* 2005, 26(23):4737-4746.

Logan, A. et al., "Decorin Attenuates Gliotic Scar Formation in the Rat Cerebral Hemisphere," *Exp. Neurol.* 1999, 159:504-510.

(56) References Cited

OTHER PUBLICATIONS

Marek, A. et al., "TGF-β-(transforming growth factor-β) in chronic inflammatory conditions—a new diagnostic and prognostic marker?" *Med. Sci. Monitl* 2002, 8(7):RA145-RA151.
Massague, J. and Chen, Y., "Controlling TGF-β signaling," *Genes and Development* 2000, 14:627-644.
Milner et al., "TSG-6: a multifunctional protein associated with inflammation," *J. Cell Sci.* 2003, 116(10):1863-1873.
Moller-Pedersen. T. et al., "Neutralizing antibody to TGF-β modulates stromal fibrosis but not regression of photoglative effect following PRK," *Curr. Eye Res.* 1998,17:736-747.
Monteleone et al., "SMAD7 in TGF-b-mediated negative regulation of gut inflammation," *Trends in Immunology* 2004, 25(10):513-517.
Mukhopadhyay et al. "Two Distinct Populations of Tumor Necrosis Factor-Stimulated Gene-6 Protein in the Extracellular Matrix of Expanded Mouse Cumulus Cell-Oocyte Complexes." *Archives of Biochemistry and Biophysics*, Oct. 1, 2001, 394(2):173-181.
Na, B. et al., "Analaysis of Human Amniotic Membrane Components as Proteinase Inhibitors for Development of Therapeutic Agent for Recalcitrant Keratitis," *Trophoblast Res.* 1999, 13:453-466.
Nakao et al., "SMAD7: a new key player in TGF-β-associated disease," *Trends in Molecular Medicine* 2002, 8(8):361-363.
Neumann et al., "High molecular weight hyaluronic acid inhibits advanced glycation endproduct-induced NF-kB activation and cytokine expression," *FEBS Ltrs.* 1999, 453:283-287.
Oikawa, J. et al. "Inhibition of Angiogenesis by 15-Deoxyspergualin." *J. Antibiotics* 1991, 44(9):1033-1035.
Ochsner et al. "Decreased Expression of Tumor Necrosis Factor-alpha-Stimulated Gene 6 in Cumulus Cells of the Cyclooxgenase-2 and EP2 Null Mice." Endocrinology, Mar. 2003, 144(3):1008-1019.
Petraglia,F. et al., "Inhibin and Activin in Human Fetal Membranes: Evidence of a Local Effect on Prostaglandin Release," *J. Clin. Endocrinol. Metab.* 1993, 77:542-548.
Prabhasawat, P. et al., "Comparison of Conjunctival Autografts, Amniotic Membrane Grafts, and Primary Closure for Pterygium Excision," *Ophthalmology* 1997, 104:974-985.
Riley, S. et al., "Production of inhibin forms by the fetal membranes, decidua, placenta and fetus at parturition," *Hum. Reprod.* 2000, 15:578-583.
Romero, R. et al., "The natural interleukin-1 receptor antagonist in the fetal, maternal, and amniotic fluid compartments: the effect of gestational age, fetal gender, and intrauterine infection," *Am. J. Obstet. Gynecol.* 1994, 171:912-921.
Ronnov-Jessen, L. et al., "Induction of α-Smooth Muscle Actin by Transforming Growth Factor-β1 in Quiescent Human Breast Gland Fibroblasts," *Lab. Invest.* 1993, 68:696-707.
Rovere et al., "The long pentraxin PTX3 binds to apoptotic cells and regulates their clearance by antigen-presenting dendritic cells," *Blood* 2000, 96(130):4300-4306.
Serini, G. et al., "The Fibronectin Domain ED-A Is Crucial for Myofibroblastic Phenotype Induction by Transforming Growth Factor-β1," *J. Cell. Biol.* 1998, 142:873-881.
Shahi, M. et al., "Control of scarring in adult wounds by neutralising antibody to transforming growth factor β," *Lancet* 1992, 339:213-214.
Singh et al., Encyclopedia of Pharmaceutical Technology, 2002, 2nd ed., pp. 751-753.
Solomon et al. "Suppression of Interleukin 1a and Interleukin 1b in Human Limbal Epithelial Cells Cultured on the Amniotic Membrane Stromal Matrix." *Br J Ophthalmol* 2001, 85:444-449.
Travis et al., "Hyaluronan Enhances Contraction of Collagen by Smooth Muscle BCells and Adventitial Fibroblasts Role of CD44 and Implications for Constrictive Remodeling," *Cir. Res.* 2001, 88:77-83 (2001).
Tseng, S. et al., "How Does Amniotic Membrane Work?" *Ocular Surface J.* 2004, 2(3):177-187.
Tseng, S. et al., "Supression of Transforming Growth Factor-Beta Isoforms, TGF-β Receptor Type II, and Myofibroblast Differentiation in Cultured Human Corneal and Limbal Fibroblasts by Amniotic Membrane Matrix," *J. Cell Physiol.*, 1999, 179:325-335.
Tseng, S. et al., "Amniotic Membrane Transplantation With or Without Limbal Allografts for Corneal Surface Reconstruction in Patients With Limbal Stem Cell Deficiency,"*Arch. Ophthalmol.* 1998, 116:431-441.
Verbeek, M. et al., "Induction of alpha-smooth muscle actin expression in cultured human brain pericytes by transforming growth factor-beta 1," *Am. J. Pathol.* 1994, 144:372-382.
Yamaguchi, Y. et al., "Negative regulation of transforming growth factor-β by the proteoglycan decorin," *Nature* 1990, 346(6281):281-284.
EP 06804232.4 Search Report mailed May 10, 2010.
PCT/US10/46675 Search Report and Written Opinion dated May 30, 2011.
PCT/US10/46675 IPRP dated Feb. 28, 2012.
PCT/US06/37906 WO Search Report dated Jul. 11, 2007.
PCT/US06/37906 IPRP dated Apr. 1, 2008.
PCT/US10/032452 WO IPRP and Written Opinion dated Oct. 25, 2011.
PCT/US10/032452 Internation Search Report mailed Dec. 27, 2010.
U.S. Appl. No. 11/528,902 Office Action mailed Dec. 16, 2009.
U.S. Appl. No. 11/529,658 Office Action mailed Dec. 16, 2009.
U.S. Appl. No. 11/535,924 Office Action mailed Dec. 16, 2009.
U.S. Appl. No. 11/529,658 Final Office Action mailed Jan. 27, 2011.
U.S. Appl. No. 11/528,980 Final Office Action mailed Aug. 11, 2009.
Li, et al. "An Experimental Study of the Effects of Human Amniotic Membrane on Human Retinal Pigment Epithelial Cell Proliferation in vitro." Acta Acadamiae Medicinae Militaris Tertia, 2003, vol. 25, No. 5, pp. 407-409 (with English Abstract).
Lieberman et al., Pharmaceutical Dosage Forms, 2 Ed. vol. 1, pp. 209-214 (1990).
Rugg, et al, "Characterization of complexes formed between TSG-6 and inter-alpha-inhibitor that act as intermediates in the covalent transfer of heavy chains onto hyaluronan," J Biol Chem, 280(27):25674-25686 (2005).
Sanggaard, et al, "The transfer of heavy chains from bikunin proteins to hyaluronan requires both TSG-6 and HC2," J Biol Chem, 283(27):18530-18537 (2008).
U.S. Appl. No. 11/528,902 Notice of Allowance mailed Mar. 7, 2012.
U.S. Appl. No. 11/528,902 Office Action mailed Jan. 27, 2011.
U.S. Appl. No. 11/528,902 Office Action mailed Apr. 2, 2009.
U.S. Appl. No. 11/528,980 Notice of Allowance mailed Feb. 23, 2012.
U.S. Appl. No. 11/528,980 Office Action mailed Jan. 10, 2011.
U.S. Appl. No. 11/528,980 Office Action mailed Oct. 15, 2010.
U.S. Appl. No. 11/528,980 Office Action mailed Nov. 13, 2008.
U.S. Appl. No. 11/528,980 Office Action mailed Aug. 11, 2009.
U.S. Appl. No. 11/529,658 Notice of Allowance mailed Mar. 8, 2012.
U.S. Appl. No. 11/529,658 Office Action mailed Apr. 3, 2009.
U.S. Appl. No. 11/529,658 Office Action mailed Sep. 3, 2010.
U.S. Appl. No. 11/535,924 Notice of Allowance mailed Mar. 20, 2012.
U.S. Appl. No. 11/535,924 Office Action mailed Jan. 31, 2011.
U.S. Appl. No. 11/535,924 Office Action mailed Mar. 31, 2009.
U.S. Appl. No. 11/535,924 Office Action mailed Sep. 8, 2010.
U.S. Appl. No. 13/453,840 Office Action mailed Aug. 21, 2012.
PCT/US2013/049983 International Search Report and Written Opinion dated Nov. 29, 2013.
Sakurai et al. Characterization of the Role of PTX2 In Enhancing The Anti-angiogenci Action of HC.HA Purified From The Chorion. Arvo Annual Meeting Abstract Search and Program Planner. 2011:4881 (May 2011).
U.S. Appl. No. 13/802,264 Office Action mailed Nov. 28, 2014.
U.S. Appl. No. 13/796,761 Office Action dated Dec. 9, 2014.
U.S. Appl. No. 13/802,359 Office Action dated Dec. 10, 2014.
Hatano et al. Transplantation of amniotic membrane and limbal autograft in the treatment of recurrent pterygium. Clinical Ophthalmology 50(6):1101-1104 (1996) (English Abstract).
Hori. Amniotic Membrane Transplantation and Immune Reaction. Folia Ophthalmologica Japonica 56(9):722-727 (2005) (English Abstract).
Jadin et al. Characterization of a Novel Recombinant Hyaluronan Binding Protein for Tissue Hyaluronan Detection. Journal of Histochemistry & Cytochemistry 62(9):672-683 (2014).

(56) References Cited

OTHER PUBLICATIONS

PCT/US2013/049983 International Preliminary Report on Patentability dated Jan. 22, 2015.
U.S. Appl. No. 13/802,447 Office Action dated Dec. 15, 2014.
Rugg, "Characterization of complexes formed between TSG-6 and inter-alpha-inhibitor that act as intermediates in the covalent transfer of heavy chains onto hyaluronan," Journal of Biological Chemistry 280: 25674-25686 (2005).
Sanctgaard et al, "The transfer of heavy chains from Bikunin proteins to hyaluronan requires both TSG-6 and IIC2," Journal of Biochemistry 283: 18530-18537 (2008).
EP10767898.9 Extended European Search Opinion dated Sep. 6, 2012.
Li, et al. "An Experimental Study of the Effects of Human Ammniotic Membrance on Human Retinal Pigment Epithelial Cell Proliferation in vitro." Acta Acadamiae Medicinae Militaris Teria, 2003, vol. 25, No. 5, pp. 407-409 (with English Abstract).

* cited by examiner

COMPOSITIONS CONTAINING HC-HA COMPLEX AND METHODS OF USE THEREOF

CROSS-REFERENCE

This application is the National Stage Entry of International Application No. PCT/US2010/032452 filed on Apr. 26, 2010, which claims the benefit of U.S. Provisional Application No. 61/172,621 filed Apr. 24, 2009, and U.S. Provisional Application No. 61/267,776 filed Dec. 8, 2009, mall of which are incorporated herein by reference in their entireties.

BACKGROUND OF THE INVENTION

The amniotic membrane (AM) is the innermost membrane enwrapping the fetus in the amniotic cavity. The AM consists of a simple epithelium, a thick basement membrane, and an avascular stroma.

SUMMARY OF THE INVENTION

Disclosed herein, in certain embodiments, is an HC•HA complex comprising hyaluronan and a heavy chain of IαI, wherein the transfer of the heavy chain of IαI is catalyzed, at least in part, by TSG-6, recombinant TSG-6, TSG-6 like protein, recombinant TSG-6 like protein, or a combination thereof. In some embodiments, the HC•HA complex comprises HC1 and HC2 of IαI. In some embodiments, the HC•HA complex has a purity of at least 75%.

Disclosed herein, in certain embodiments, is an HC•HA complex comprising hyaluronan and a heavy chain of IαI, wherein the transfer of the heavy chain of IαI is catalyzed by the TSG-6 like protein and/or a recombinant TSG-6 like protein. In some embodiments, the HC•HA complex comprises HC1 and HC2 of IαI. In some embodiments, the HC•HA complex has a purity of at least 75%.

Disclosed herein, in certain embodiments, is a method of reducing or preventing inflammation, comprising administering an HC•HA disclosed herein to an individual in need thereof. In some embodiments, the HC•HA complex is produced by contacting (a) hyaluronan, (b) a heavy chain of IαI, and (c) TSG-6. In some embodiments, the HC•HA complex is produced by contacting (a) hyaluronan, (b) HC1 and HC2 of IαI, and (c) TSG-6. In some embodiments, the HC•HA complex is produced by contacting (a) hyaluronan, (b) a heavy chain of IαI, and (c) the TSG-6 like protein. In some embodiments, the HC•HA complex is produced by contacting (a) hyaluronan, (b) HC1 and HC2 of IαI, and (c) the TSG-6 like protein. In some embodiments, the method further comprises administering an additional anti-inflammatory agent. In some embodiments, the method further comprises administering an additional antibiotic agent.

Disclosed herein, in certain embodiments, is a method of reducing or preventing scarring comprising administering an HC•HA complex of any of claims 1-6 to an individual in need thereof. In some embodiments, the HC•HA complex is produced by contacting (a) hyaluronan, (b) a heavy chain of IαI, and (c) TSG-6. In some embodiments, the HC•HA complex is produced by contacting (a) hyaluronan, (b) HC1 and HC2 of IαI, and (c) TSG-6. In some embodiments, the HC•HA complex is produced by contacting (a) hyaluronan, (b) a heavy chain of IαI, and (c) the TSG-6 like protein. In some embodiments, the HC•HA complex is produced by contacting (a) hyaluronan, (b) HC1 and HC2 of IαI, and (c) the TSG-6 like protein. In some embodiments, the method further comprises administering an additional anti-inflammatory agent. In some embodiments, the method further comprises administering an additional antibiotic agent.

Disclosed herein, in certain embodiments, is a method of reducing or preventing angiogenesis comprising administering an HC•HA complex of any of claims 1-6 to an individual in need thereof. In some embodiments, the HC•HA complex is produced by contacting (a) hyaluronan, (b) a heavy chain of IαI, and (c) TSG-6. In some embodiments, the HC•HA complex is produced by contacting (a) hyaluronan, (b) HC1 and HC2 of IαI, and (c) TSG-6. In some embodiments, the HC•HA complex is produced by contacting (a) hyaluronan, (b) a heavy chain of IαI, and (c) the TSG-6 like protein. In some embodiments, the HC•HA complex is produced by contacting (a) hyaluronan, (b) HC1 and HC2 of IαI, and (c) the TSG-6 like protein. In some embodiments, the method further comprises co-administering an additional chemotherapeutic agent.

Disclosed herein, in certain embodiments, is a method of preventing transplant rejection comprising contacting a tissue or a plurality of cells with an HC•HA complex of any of claims 1-6. In some embodiments, the method further comprises contacting the tissue or plurality of cells with reperfusion solution. In some embodiments, the HC•HA complex is produced by contacting (a) hyaluronan, (b) a heavy chain of IαI, and (c) TSG-6. In some embodiments, the HC•HA complex is produced by contacting (a) hyaluronan, (b) HC1 and HC2 of IαI, and (c) TSG-6. In some embodiments, the HC•HA complex is produced by contacting (a) hyaluronan, (b) a heavy chain of IαI, and (c) the TSG-6 like protein. In some embodiments, the HC•HA complex is produced by contacting (a) hyaluronan, (b) HC1 and HC2 of IαI, and (c) the TSG-6 like protein. In some embodiments, the method further comprises co-administering an additional immunosuppressive agent.

Disclosed herein, in certain embodiments, is a method of manufacturing an HC•HA complex comprising, contacting (a) HA; (b) HC1 and HC2 of IαI, wherein at least one of HC1 and HC2 is optionally recombinant; and (c) TSG-6 or TSG-6 like protein, wherein the TSG-6 or TSG-6 like protein is optionally recombinant. In some embodiments, the method further comprises a bioreactor. In some embodiments, the method further comprises a plurality of cells wherein the cells are engineered to constitutively express TSG-6 or TSG-6 like protein. In some embodiments, the method further comprises a plurality of cells wherein the cells are engineered to constitutively express HC1, HC2, or both.

Disclosed herein, in certain embodiments, is a method of isolating HC•HA from amniotic material comprising: (a) processing the amniotic material such that it is suitable for extraction of an HC•HA complex; and (b) extracting HC•HA complex by a method selected from: chromatography, gel filtration, centrifugation, or differential solubility, ethanol precipitation, or combinations thereof. In some embodiments, the processing comprises homogenizing the amniotic material. In some embodiments, the method further comprises extracting the HC•HA complex by gradient centrifugation. In some embodiments, the processing occurs at below ambient temperature. In some embodiments, the processing occurs at 4° C. In some embodiments, the amniotic material is amniotic membrane. In some embodiments, the amniotic material is chorionic membrane.

DESCRIPTION OF DRAWINGS

FIG. 8B, an MTT assay, shows that there is no difference in cell viability between the control (Ctrl) and HMW HA (P=0.1). In contrast, HUVEC viability was significantly suppressed by an HC•HA complex when compared to the control or HMW HA (P=0.01 or 0.003, respectively). FIGS. 8C and 8D show that proliferation is inhibited. There was no significant difference in percentage of BrdU positive nuclei between the control (32.5%, n=133) or 5 μg/ml HWW HA added for 48 h (31.9%, n=144) and in the labeling index (i.e., the percentage of proliferating cells) HMW HA) (P=0.9). In contrast, BrdU labeling was completely abolished when HUVEC cells were added with 5 μg/ml HC•HA complex, resulting in a significant reduction of the labeling index (1.9%, n=69), which was significantly different from Ctrl and HMW HA (P=0.00005 and P=0.001, respectively). Finally, FIG. 8E shows that cell death increases. The Live & Dead assay showed live HUVEC cells in control with or without addition of 25 μg/ml HMW HA. In contrast, notable reduction of live cells and increase of dead cells were caused by 25 μg/ml HC•HA complex.

DETAILED DESCRIPTION OF THE INVENTION

Figure 1:
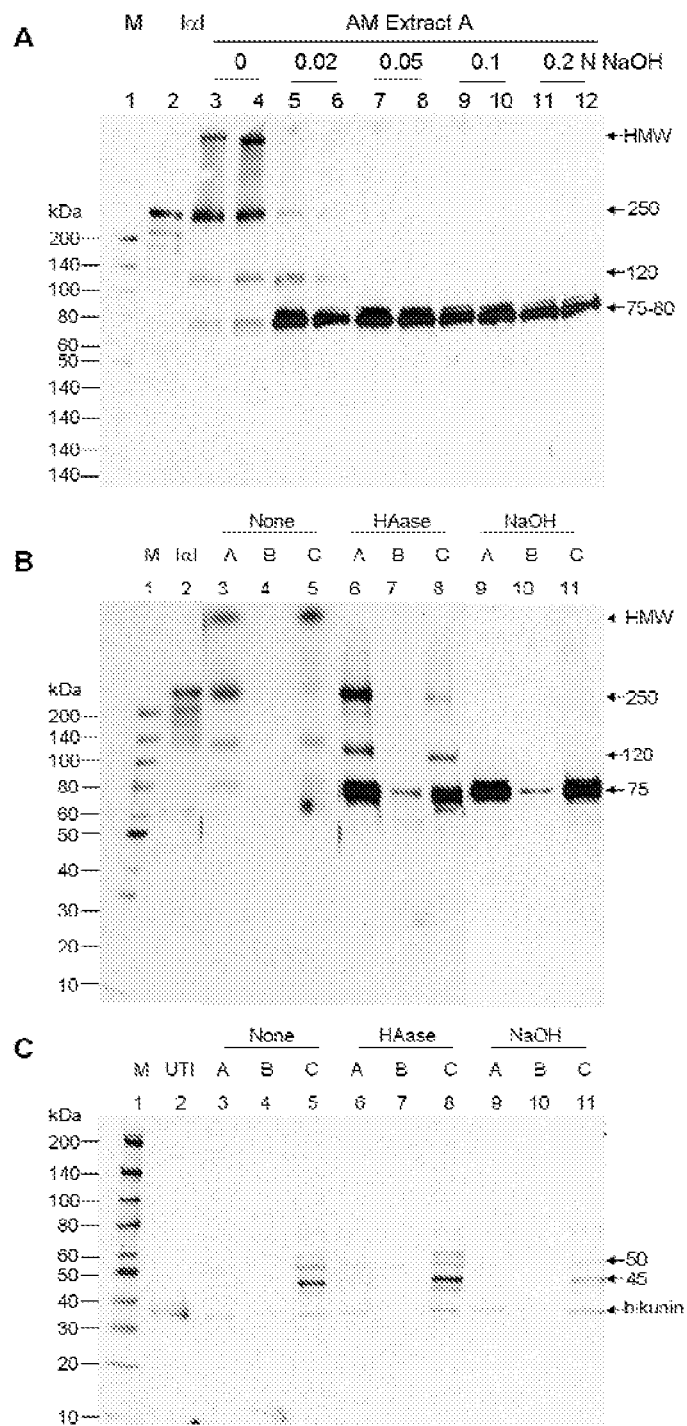
FIG. 1: Extract A was treated (in duplicate) with a series of NaOH concentrations (0, 0.02, 0.05, 0.10, 0.2 N) before Western blotting with an anti-IαI antibody to determine the optimal NaOH concentration for cleaving linkage between HA and HCs (A, M: protein ladder markers and IαI: purified from the human plasma). Extracts A, B, and C with or without HAase digestion or 0.05 N NaOH treatment were analyzed (B). Bikunin was not associated with HA in AM extracts when the same samples as described in B were analyzed by Western blot with an anti-bikunin antibody (C, purified urine bikunin, i.e., UTI, as the control).
Figure 1:
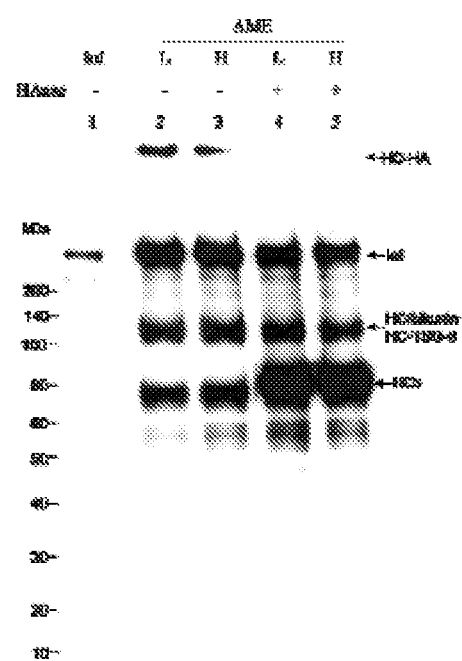

Disclosed herein, in certain embodiments, are HC•HA complexes. In some embodiments, an HC•HA complex is reconstituted HC•HA complex (i.e., manufactured; hereinafter "rcHC•HA"). In some such embodiments, the rcHC•HA comprises one or more recombinant components (e.g., recombinant HC1 or recombinant HC2). Also, disclosed herein, in certain embodiments, are HC•HA complexes that have been isolated and purified from amniotic material, including amniotic membrane, amniotic fluid or chorionic membrane (hereinafter "nHC•HA"). Such amniotic material is preferably mammalian amniotic material, and more preferably human amniotic material. In some embodiments, the amniotic material is human amniotic membrane. In some embodiments, the amniotic material is human chorionic membrane. Also disclosed herein are formulations of HC•HA complexes that include both rcHC•HA and nHC•HA.

Disclosed herein, in certain embodiments, is a method of manufacturing an HC•HA complex. In some embodiments, the agent that facilitates the transfer of, catalyzes the transfer of, and/or transfers a heavy chain (hereinafter HC) of IαI onto HA is selected from TSG-6; recombinant TSG-6; a biological material obtained from water soluble and water insoluble amniotic membrane extracts that contains TSG-6 or a 50 kDa material as determined by a Western blot using anti-TSG-6 antibodies (hereinafter, the "TSG-6 like protein"); a recombinant form of the TSG-6 like protein; or combinations thereof. In some embodiments, TSG-6 or TSG-6-like protein is obtained from cultures of human amniotic epithelial cells or amniotic stromal mesenchymal cells. In some embodiments, rcHC•HA is manufactured using (a) HA; (b) recombinant inter-alpha-trypsin inhibitor (IαI), recombinant HC1, recombinant HC2, or combinations thereof and (c) TSG-6 or TSG-6 like protein, wherein the TSG-6 or TSG-6 like protein is optionally recombinant. In some embodiments, rcHC•HA is manufactured using (a) HA; (b) IαI from serum, wherein the IαI is optionally purified from the serum; (c) TSG-6 or TSG-6 like protein, wherein the TSG-6 or TSG-6 like protein is optionally recombinant. The manufactured HC•HA complex is at least 25% purified from other components of the manufacturing process; at least 50% purified from other components of the manufacturing process; at least 75% purified from other components of the manufacturing process; or at least 90% purified from other components of the manufacturing process.

Further disclosed herein, in certain embodiments, are methods of reconstituting HC•HA. In some embodiments, rcHC•HA is obtained by contacting (a) HA; (b) HC1 and HC2 of IαI, wherein at least one of HC1 and HC2 is optionally recombinant; and (c) TSG-6 or TSG-6 like protein, wherein the TSG-6 or TSG-6 like protein is optionally recombinant. In some embodiments, the method further comprises a plurality of cells wherein the cells are engineered to constitutively express TSG-6 or TSG-6 like protein. In some embodiments, the method further comprises a plurality of cells wherein the cells are engineered to constitutively express HC1, HC2, or both. In some embodiments, the source of the HA, HC1 and HC2 of IαI, and TSG-6 or TSG-6 like protein is any combination of the sources disclosed in Table 1. However, the list is not intended to be exclusive, only exemplary. The source of the source of the HA, HC1 and HC2 of IαI, and TSG-6 or TSG-6 like protein is any suitable source. The manufactured HC•HA complex is at least 25% purified from other components of the reconstituting process; at least 50% purified from other components of the reconstituting process; at least 75% purified from other components of the reconstituting process; or at least 90% purified from other components of the reconstituting process.

TABLE 1

| Component | Source |
| --- | --- |
| HA | Commercially available powder |
|  | HAS1, HAS2, or HAS3 expressing cells |
| HC1 | Unpurified serum |
|  | Purified from serum |
|  | Recombinant cells |
| HC2 | Unpurified serum |
|  | Purified from serum |
|  | Recombinant cells |
| TSG-6 | Amniotic material extract |
|  | Amniotic stromal mesenchymal cells |
|  | Human amniotic epithelial cells |
|  | Recombinant cells |
| TSG-6 like protein | Amniotic material extract |
|  | Amniotic stromal mesenchymal cells |
|  | Human amniotic epithelial cells |
|  | Recombinant cells |

Additionally, disclosed herein, in certain embodiments, are methods of isolating HC•HA from amniotic material. In some embodiments, the method comprises (a) processing the amniotic material such that it is suitable for extraction of an HC•HA complex; and (b) extracting HC•HA complex by a method selected from: chromatography, gel filtration, centrifugation, or differential solubility, ethanol precipitation, or combinations thereof. In some embodiments, the processing comprises homogenizing the amniotic material. In some embodiments, the processing occurs at below ambient temperature. The manufactured HC•HA complex is at least 25% purified from other components of the isolation process; at least 50% purified from other components of the isolation process; at least 75% purified from other components of the isolation process; or at least 90% purified from other components of the isolation process. In some embodiments, the amniotic material is amniotic membrane. In some embodiments, the amniotic material is chorionic membrane.

Also disclosed herein is a method of reducing or preventing inflammation, comprising administering an HC•HA complex disclosed herein to an individual in need thereof. In some embodiments, the method comprises the use of nHC•HA and/or rcHC•HA. In some embodiments, the method comprises the use of nHC•HA. In some embodiments, the method comprises the use of reconstituted HC•HA (rcHC•HA). In some embodiments, at least one heavy chain of rcHC•HA is recombinant (e.g., HC1 is from a recombinant source, HC2 is from a recombinant source, or both are from recombinant sources).

Further disclosed herein, is a method of reducing or preventing scarring comprising administering an HC•HA complex disclosed herein to an individual in need thereof. In some embodiments, the method comprises the use of nHC•HA and/or rcHC•HA. In some embodiments, the method comprises the use of nHC•HA. In some embodiments, the method comprises the use of reconstituted HC•HA (rcHC•HA). In some embodiments, at least one heavy chain of rcHC•HA is recombinant (e.g., HC1 is from a recombinant source, HC2 is from a recombinant source, or both are from recombinant sources).

Disclosed herein, in certain embodiments, is a method of reducing or preventing angiogenesis comprising administering an HC•HA complex disclosed herein to an individual in need thereof. In some embodiments, the method comprises the use of nHC•HA and/or rcHC•HA. In some embodiments, the method comprises the use of nHC•HA. In some embodiments, the method comprises the use of reconstituted HC•HA (rcHC•HA). In some embodiments, at least one heavy chain of rcHC•HA is recombinant (e.g., HC1 is from a recombinant source, HC2 is from a recombinant source, or both are from recombinant sources).

Additionally, disclosed herein, in certain embodiments, is a method of preventing transplant rejection comprising contacting a plurality of cells (e.g., stem cells, an organ, or a tissue graft) with an HC•HA complex. In some embodiments, the method comprises the use of nHC•HA and/or rcHC•HA. In some embodiments, the method comprises the use of nHC•HA. In some embodiments, the method comprises the use of reconstituted HC•HA (rcHC•HA). In some embodiments, at least one heavy chain of rcHC•HA is recombinant (e.g., HC1 is from a recombinant source, HC2 is from a recombinant source, or both are from recombinant sources).

Certain Terminology

Unless defined otherwise, all technical and scientific terms used herein have the same meaning as is commonly understood by one of skill in the art to which the claimed subject matter belongs.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, (e.g., "include", "includes", and "included" is not limiting.

The term "isolated," as used herein, refers to separating and removing a component of interest from components not of interest. Isolated substances can be in either a dry or semi-dry state, or in solution, including but not limited to an aqueous solution. The isolated component can be in a homogeneous state or the isolated component can be a part of a pharmaceutical composition that comprises additional pharmaceutically acceptable carriers and/or excipients. Purity and homogeneity may be determined using analytical chemistry techniques including, but not limited to, polyacrylamide gel electrophoresis or high performance liquid chromatography. In addition, when a component of interest is isolated and is the predominant species present in a preparation, the component is described herein as substantially purified. By way of example only, proteins are "isolated" when such proteins are free of at least some of the cellular components with which it is associated in the natural state, or that the protein has been concentrated to a level greater than the concentration of its in vivo or in vitro production.

The term "purified," as used herein, refers to a component of interest which is at least 85% pure, at least 90% pure, at least 95% pure, at least 99% or greater pure.

The term "subject", "individual" or "individual" as used herein encompasses mammals and non-mammals. None of the terms are to be construed as requiring the supervision of a medical professional (e.g., a physician, nurse, orderly, hospice worker). In one embodiment of the methods and compositions provided herein, the mammal is a human.

The terms "treat," "treating" or "treatment," and other grammatical equivalents mean slowing or stopping the development of a disorder, causing regression of a disorder, ameliorating a disorder, the symptoms of a disorder, preventing the development or presentation of additional symptoms, ameliorating and/or preventing the underlying cause of a symptom, or combinations thereof. The term further includes achieving a prophylactic benefit. For prophylactic benefit, an HC•HA complex or composition disclosed herein is administered to an individual at risk of developing a particular disorder, predisposed to developing a particular disorder, or to an individual reporting one or more of the physiological symptoms of a disorder.

The terms "effective amount", "therapeutically effective amount" or "pharmaceutically effective amount" as used herein, refer to an amount of an HC•HA complex that is sufficient to treat a disorder. In some embodiments, the result is a reduction in and/or alleviation of the signs, symptoms, or causes of a disorder, or any other desired alteration of a biological system. For example, an "effective amount" for therapeutic uses is the amount of the composition comprising an HC•HA complex as disclosed herein required to provide a clinically significant decrease in a disorder. An appropriate "effective" amount in any individual case is determined using any suitable technique, (e.g., a dose escalation study).

The term "pharmaceutically acceptable" as used herein, refers to a material, (e.g., a carrier or diluent), which does not abrogate the biological activity or properties of an HC•HA complexes described herein, and is relatively nontoxic (i.e., the material is administered to an individual without causing undesirable biological effects or interacting in a deleterious manner with any of the components of the composition in which it is contained).

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions are achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Cassol et al. (1992); Rossolini et al., Mol. Cell. Probes 8:91-98 (1994)).

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to agents that have the same basic chemical structure as a naturally occurring amino acid, i.e., an α carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

The terms "polypeptide", peptide" and "protein" are used interchangeably herein to refer to a polymer of amino acid residues. The terms apply to naturally occurring amino acid polymers as well as amino acid polymers in which one or more amino acid residues is a non-naturally occurring amino acid, e.g., an amino acid analog. The terms encompass amino acid chains of any length, including full length proteins, wherein the amino acid residues are linked by covalent peptide bonds.

To determine the percent homology of two amino acid sequences or of two nucleic acids, the sequences can be aligned for optimal comparison purposes (e.g., gaps are introduced in the sequence of a first amino acid or nucleic acid sequence for optimal alignment with a second amino or nucleic acid sequence). The amino acid residues or nucleotides at corresponding amino acid positions or nucleotide positions can then be compared. When a position in the first sequence is occupied by the same amino acid residue or nucleotide as the corresponding position in the second sequence, then the molecules are identical at that position. The percent homology between the two sequences is a function of the number of identical positions shared by the sequences (i.e., % identity=# of identical positions/total # of positions (e.g., overlapping positions)×100). In some embodiments the two sequences are the same length.

To determine percent homology between two sequences, the algorithm of Karlin and Altschul (1990) Proc. Natl. Acad. Sci. USA 87:2264-2268, modified as in Karlin and Altschul (1993) Proc. Natl. Acad. Sci. USA 90:5873-5877 is used. Such an algorithm is incorporated into the NBLAST and XBLAST programs of Altschul, et al. (1990) J. Mol. Biol. 215:403-410. BLAST nucleotide searches are performed with the NBLAST program, score=100, wordlength=12 to obtain nucleotide sequences homologous to a nucleic acid molecules described or disclose herein. BLAST protein searches are performed with the XBLAST program, score=50, wordlength=3. To obtain gapped alignments for comparison purposes, Gapped BLAST is utilized as described in Altschul et al. (1997) Nucleic Acids Res. 25:3389-3402. When utilizing BLAST and Gapped BLAST programs, the default parameters of the respective programs (e.g., XBLAST and NBLAST) are used. See the website of the National Center for Biotechnology Information for further details (on the World Wide Web at ncbi.nlm.nih.gov). Proteins suitable for use in the methods described herein also includes proteins having between 1 to 15 amino acid changes, e.g., 1, 2, 3, 4, 5, 6, 7, 8, 9, 10, 11, 12, 13, 14, or 15 amino acid substitutions, deletions, or additions, compared to the amino acid sequence of any protein described herein. In other embodiments, the altered amino acid sequence is at least 75% identical, e.g., 77%, 80%, 82%, 85%, 88%, 90%, 92%, 95%, 97%, 98%, 99%, or 100% identical to the amino acid sequence of any protein inhibitor described herein. Such sequence-variant proteins are suitable for the methods described herein as long as the altered amino acid sequence retains sufficient biological activity to be functional in the compositions and methods described herein. Where amino acid substitutions are made, the substitutions should be conservative amino acid substitutions. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff et al (1992), Proc. Natl Acad. Sci. USA, 89:10915-10919). Accordingly, the BLOSUM62 substitution frequencies are used to define conservative amino acid substitutions that, in some embodiments, are introduced into the amino acid sequences described or disclosed herein. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Figure 2:
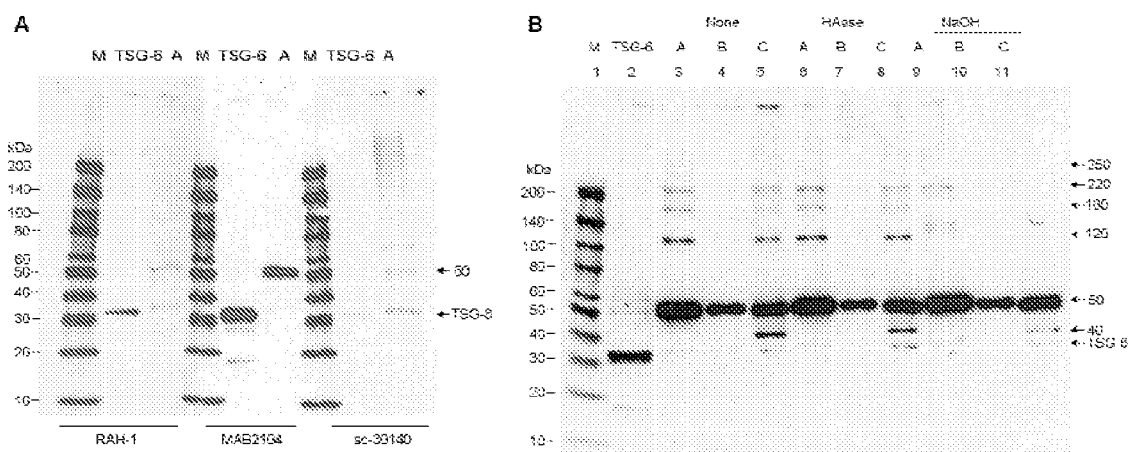
FIG. 2. TSG-6 and TSG-6 like proteins were found to be present in Extract A using three different antibodies that recognized the control TSG-6Q (25 ng) as a ~32-kDa protein (A, Bands of ~35-kDa and ~50-kDa were seen in Extract A). TSG-6 was not covalently coupled with HA in Extracts A, B, C that were treated with or without HAase or NaOH and analyzed by Western blots with anti-TSG-6 antibody MAB2104 (B). The TSG-6-like protein was found to be different from TSG-6 in the molecular weight, and specifically produced by the amniotic membrane.

As used herein, "the TSG-6 like protein" means a biological material obtained from amniotic membrane that presents a 50 kDa band in a Western blot of water soluble and water insoluble amniotic membrane extracts using anti-TSG-6 antibodies. See FIG. 2. In certain instances, TSG-6 like protein is only found in the amniotic membrane and produced by amniotic epithelial cells or amniotic stromal mesenchymal cells.

As used herein, "recombinant TSG-6" means a TSG-6 protein that is produced by recombinant methods (i.e., the TSG-6 gene from a first source (e.g., a human TSG-6 gene) is cloned into a DNA molecule from a second source (e.g., a bacterial plasmid)), As used herein, "recombinant TSG-6 like protein" means a TSG-6 like protein that is produced by recombinant methods (i.e., the TSG-6 like gene from a first source (e.g., a human TSG-6 like gene) is cloned into a DNA molecule from a second source (e.g., a bacterial plasmid)), As used herein, "recombinant HC1" means an HC1 protein that is produced by recombinant methods (i.e., the HC1 gene from a first source (e.g., a human HC1 gene) is cloned into a DNA molecule from a second source (e.g., a bacterial plasmid)), As used herein, "recombinant HC2" means an HC2 protein that is produced by recombinant methods (i.e., the HC2 gene from a first source (e.g., a human HC2 gene) is cloned into a DNA molecule from a second source (e.g., a bacterial plasmid)), As used herein, the term "bioreactor" refers to any artificial container in which mammalian cells grow. In some embodiments, a bioreactor is 1 liter, 10 liters, 100 liters, 250 liters, 500 liters, 1000 liters, 2500 liters, 5000 liters, 8000 liters, 10,000 liters, or 12,000 liters. A bioreactor is composed of any material that is suitable for holding mammalian cell cultures suspended in media (e.g., glass, plastic or metal).

As used herein, the "production bioreactor" is the bioreactor in which the final HC•HA complex disclosed herein is reconstituted.

HC•HA

As used herein, "hyaluronan" (or "HA") means a substantially non-sulfated or non-sulfated glycosaminoglycan with linear repeating disaccharide units of glucuronosyl-N-acetyl-glucosamine. In some embodiments, HA is obtained from a commercial supplier (e.g., Sigma Aldrich or Abbott Medical Optics, Irvine, Calif.). In some embodiments, HA is obtained from a commercial supplier as a powder. In some embodiments, HA is obtained from a cell that expresses a hyaluronan synthases (e.g., HAS1, HAS2, and HAS3). In certain instances, an HA synthase lengthens hyaluronan by repeatedly adding glucuronic acid and N-acetylglucosamine to the nascent polysaccharide as it is extruded through the cell membrane into the extracellular space.

In certain instances, high molecular weight (HMW) HA promotes cell quiescence and structural integrity of such tissues as the cartilage and the vitreous body (humor) in the eye, and is associated with scarless fetal wound healing. In certain instances, HMW HA inhibits the gene expression of pro-inflammatory mediators and pro-angiogenesis.

In certain instances, HMW HA is degraded into smaller fragments and oligosaccharides (e.g., via hyaluronase or free radical oxidation) conditions. In certain instances, LMW HA stimulate vascular endothelial cell proliferation, migration, collagen synthesis, sprout formation, and angiogenesis in rat skin, myocardial infarction, and cryo-injured skin graft model by promoting the gene expression of pro-inflammatory and pro-angiogenic mediators.

In certain instances, HA forms a covalent complex with the heavy chains (HC) of inter-α-inhibitor (IαI) by covalently binding to the heavy chains (hereinafter, "HC•HA"). (See FIG. 1). In certain instances, IαI consists of two heavy chains (HC1 and HC2), both of which are linked through ester bonds to a chondroitin sulfate chain that is attached to the light chain (i.e., Bikunin)

In certain instances, the TSG-6 or TSG-6 like protein facilitates the transfer of, catalyzes the transfer of, and/or transfers the HC1 and HC2 of IαI to HA. In certain instances, the expression of TSG-6 is induced by inflammatory mediators such as TNF-α and interleukin-1 In certain instances, the expression of TSG-6 like protein is independent of inflammatory mediators such as TNF-α.

Methods of Treatment

A. Scarring

Described herein, in certain embodiments, is a method of preventing, reducing, or reversing scarring in a subject in need thereof, comprising administering to the subject a composition comprising an HC•HA complex (e.g., nHC•HA and/or rcHC•HA) disclosed herein.

As used herein, "scarring" refers to the formation of a scar. In one aspect, the scar is a hypertrophic scar, or keloid scar, or a scar resulting from acne. As used herein, a "scar" is an area of fibrous tissue that results from the overproduction of collagen. In certain instances, wound healing comprises the migration of fibroblasts to the site of injury. In certain instances, fibroblasts deposit collagen. In certain instances, fibroblasts deposit excess collagen at the wound site, resulting in a scar.

In certain instances, an HC•HA complex disclosed herein (e.g., nHC•HA and/or rcHC•HA) prevents or inhibits TGF-β signaling. In certain instances, TGF-β regulates the extracellular matrix by stimulating fibroplasia and collagen deposition and inhibiting extracellular matrix degradation (by up-regulating the synthesis of protease inhibitors). In certain instances, preventing or inhibiting the expression of TGF-β results in the prevention of or a reduction in intensity of a scar. In some embodiments, administering an HC•HA complex disclosed herein (e.g., nHC•HA and/or rcHC•HA) prevents or reduces scarring.

In some embodiments, an HC•HA complex disclosed herein (e.g., nHC•HA and/or rcHC•HA) inhibits or prevents the ability of fibroblasts to differentiate into myofibroblasts. In some embodiments, an HC•HA complex disclosed herein (e.g., nHC•HA and/or rcHC•HA) reverts differentiated myofibroblasts to fibroblasts.

In some embodiments, a method disclosed herein is used to prevent, reduce or reverse the formation of a scar. In some embodiments, a method disclosed herein comprises administering an HC•HA complex disclosed herein (e.g., nHC•HA and/or rcHC•HA) to an individual with a disorder that results in scarring (e.g., dermatitis). In some embodiments, a method disclosed herein comprises administering an HC•HA complex disclosed herein (e.g., nHC•HA and/or rcHC•HA) to an individual in need thereof before or after trauma. In some embodiments, a method disclosed herein comprises administering an HC•HA complex disclosed herein (e.g., nHC•HA and/or rcHC•HA) to an individual in need thereof before or after surgery.

In some embodiments, a method disclosed herein is used to prevent or reduce the formation of a scar on an eye or on the surrounding tissue. In some embodiments, a method disclosed herein comprises administering an HC•HA complex disclosed herein (e.g., nHC•HA and/or rcHC•HA) to an individual with a disorder that results in scarring of the eye or surrounding tissue (e.g., retinopathy of prematurity). In some embodiments, a method disclosed herein comprises administering an HC•HA complex disclosed herein (e.g., nHC•HA and/or rcHC•HA) to an individual in need thereof before or after trauma to an eye or the surrounding tissue. In some embodiments, a method disclosed herein comprises administering an HC•HA complex disclosed herein (e.g., nHC•HA and/or rcHC•HA) to an individual in need thereof before or after surgery to an eye or the surrounding tissue.

B. Inflammation

Described herein, in certain embodiments, is a method of preventing or reducing inflammation in a subject in need thereof, comprising administering to the subject a composition comprising an HC•HA complex (e.g., nHC•HA and/or rcHC•HA) disclosed herein. As used herein, "inflammation" means physiological responses resulting from the migration of plasma and/or leukocytes (e.g., lymphocytes, macrophages, granulocytes, and neutrophils) to the site of an infection or trauma (e.g., blunt force trauma, penetrating trauma, or surgery).

In certain instances, leukocytes secrete cytokines following contact with an antigen. As used herein, "cytokines" are signaling proteins or glycoproteins. In certain instances, a cytokine binds to a cell-surface receptor. In certain instances, cytokines induces the chemotaxis of leukocytes to the site of an infection. In certain instances, cell surface receptors on a leukocyte detect chemical gradients of a cytokine. In certain instances, a leukocyte follows the gradient to the site of infection. In certain instances, the binding of a cytokine to a cell-surface receptor results in the upregulation or downregulation of certain genes and their transcription factors. In certain instances, changes in gene expression results in the production of cytokines, an increase in the production of cytokines, or an increase in the presentation of cell surface receptors.

By way of non-limiting example, cytokines include interleukins IL-1, IL-6, IL-8, MCP-1 (also known as CCL2), and TNF-α. Interleukin 1 is present in the body in two isoforms: IL-1α and IL-1β. In certain instances, the presence of IL-1 increases the expression of adhesion factors on endothelial cells. This, in turn, enables the transmigration of leukocytes to the site of infection. In certain instances, IL-8 induces the chemotaxis of leukocytes. In certain instances, TNF-α induces the chemotaxis of leukocytes. In certain instances, MCP-1 recruits leukocytes to sites of tissue injury and infection.

In some embodiments, an HC•HA complex disclosed herein (e.g., nHC•HA and/or rcHC•HA) suppresses the production of and/or activity of cytokines. In certain instances, a decrease in the concentration cytokines reduces or prevents inflammation by decreasing the number of leukocytes and/or the rate at which leukocytes migrate to the site of an injury.

In some embodiments, an HC•HA complex disclosed herein (e.g., nHC•HA and/or rcHC•HA) induces apoptosis of a leukocyte (e.g., a macrophage, neutrophil, or lymphocyte). In some embodiments, an HC•HA complex disclosed herein (e.g., nHC•HA and/or rcHC•HA) decreases the number of activated leukocytes or the rate at which leukocytes are activated. In certain instances, a decrease in the concentration of leukocytes reduces or prevents inflammation by decreasing the number (e.g., facilitate death of such cells via apoptosis) of cells that migrate to the site of an injury.

In some embodiments, the inflammatory disorder is an autoimmune disorder, an allergy, a leukocyte defect, graft versus host disease, tissue transplant rejection, or combinations thereof. In some embodiments, the inflammatory disorder is a bacterial infection, a protozoal infection, a protozoal infection, a viral infection, a fungal infection, or combinations thereof. In some embodiments, the inflammatory disorder is a T-cell mediated inflammatory disorder. In some embodiments, the inflammatory disorder is a macrophage mediated inflammatory disorder. In some embodiments, the inflammatory disorder is a Th-17 mediated immune disorder. In some embodiments, the inflammatory disorder is Acute disseminated encephalomyelitis; Addison's disease; Ankylosing spondylitis; Antiphospholipid antibody syndrome; Autoimmune hemolytic anemia; Autoimmune hepatitis; Autoimmune inner ear disease; Bullous pemphigoid; Chagas disease; Chronic obstructive pulmonary disease; Coeliac disease; Dermatomyositis; Diabetes mellitus type 1; Diabetes mellitus type 2; Endometriosis; Goodpasture's syndrome; Graves' disease; Guillain-Barré syndrome; Hashimoto's disease; Idiopathic thrombocytopenic purpura; Interstitial cystitis; Systemic lupus erythematosus (SLE); Metabolic syndrome, Multiple sclerosis; Myasthenia gravis; Myocarditis, Narcolepsy; Obesity; Pemphigus Vulgaris; Pernicious anaemia; Polymyositis; Primary biliary cirrhosis; Rheumatoid arthritis; Schizophrenia; Scleroderma; Sjögren's syndrome; Vasculitis; Vitiligo; Wegener's granulomatosis; Allergic rhinitis; Prostate cancer; Non-small cell lung carcinoma; Ovarian cancer; Breast cancer; Melanoma; Gastric cancer; Colorectal cancer; Brain cancer; Metastatic bone disorder; Pancreatic cancer; a Lymphoma; Nasal polyps; Gastrointestinal cancer; Ulcerative colitis; Crohn's disorder; Collagenous colitis; Lymphocytic colitis; Ischaemic colitis; Diversion colitis; Behçet's syndrome; Infective colitis; Indeterminate colitis; Inflammatory liver disorder, Endotoxin shock, Septic shock; Rheumatoid spondylitis, Ankylosing spondylitis, Gouty arthritis, Polymyalgia rheumatica, Alzheimer's disorder, Parkinson's disorder, Epilepsy, AIDS dementia, Asthma, Adult respiratory distress syndrome, Bronchitis, Cystic fibrosis, Acute leukocyte-mediated lung injury, Distal proctitis, Wegener's granulomatosis, Fibromyalgia, Bronchitis, Cystic fibrosis, Uveitis, Conjunctivitis, Psoriasis, Eczema, Dermatitis, Smooth muscle proliferation disorders, Meningitis, Shingles, Encephalitis, Nephritis, Tuberculosis, Retinitis, Atopic dermatitis, Pancreatitis, Periodontal gingivitis, Coagulative Necrosis, Liquefactive Necrosis, Fibrinoid Necrosis, Neointimal hyperplasia, or combinations thereof.

In some embodiments, the inflammatory disorder is an inflammatory disorder of an eye or the surrounding tissue. In some embodiments, the inflammatory disorder is conjunctivitis. In certain instances, conjunctivitis results from exposure to an allergen. In certain instances, conjunctivitis results from a bacterial infection. In some embodiments, the inflammatory disorder is keratitis. As used herein, "keratitis" is a disorder characterized by inflammation of the cornea. In some embodiments, the inflammatory disorder is keratoconjunctivitis (i.e., a combination of conjunctivitis and keratitis (i.e., corneal inflammation)). In some embodiments, the inflammatory disorder is blepharitis. As used herein, "blepharitis" is an ophthalmic disorder characterized by inflammation of the eyelid margins. In some embodiments, the inflammatory disorder is blepharoconjunctivitis (i.e., a combination of conjunctivitis and blepharitis (i.e., inflammation of an eyelid)). In some embodiments, the inflammatory disorder is scleritis. As used herein, "scleritis" is a disorder characterized by inflammation of the sclera. In some embodiments, the inflammatory disorder is episcleritis. As used herein, "episcleritis" is an inflammatory disorder of the episclera characterized by hyperaemia, and chemosis. In some embodiments, the inflammatory disorder is uveitis. As used herein, "uveitis" is an inflammatory disorder of the uvea. In some embodiments, the disorder is retinitis. As used herein, "retinitis" is an inflammatory disorder of a retina. In some embodiments, the disorder is choroiditis. As used herein, "choroiditis" is an inflammatory disorder of the uvea, ciliary body and the choroid.

C. Angiogenesis

Disclosed herein, in certain embodiments, is a method of preventing or reducing angiogenesis in a subject in need thereof, comprising administering to the subject a composition comprising an HC•HA complex (e.g., nHC•HA and/or rcHC•HA) disclosed herein. As used herein, "angiogenesis" means the formation of new blood vessels. In certain instances, angiogenesis facilitates the growth and metastasis of a tumor. Further, in certain instances, abnormal angiogenesis is the basis of wet age-related macular degeneration (wARMD) and diabetic proliferative retinopathy. In certain instances, an HC•HA complex (e.g., nHC•HA and/or rcHC•HA) disclosed herein prevents or reduces angiogenesis.

In certain instances, the binding of a ligand to the VEGF receptor-2 (VEGFR-2) starts a tyrosine kinase signaling cascade that stimulates the production of factors that variously stimulate vessel permeability (eNOS, producting NO), proliferation/survival (bFGF), migration (ICAMs/VCAMs/MMPs) and finally differentiation into mature blood vessels. In certain instances, following binding of VEGFR-2 to its ligand, endothelial cells form tube structures resembling capillaries.

As used herein, "wet Age Related Macular Degeneration", "wARMD", or "wet ARMD" means a disorder of an eye characterized by the proliferation of blood vessels from the choroid. In certain instances, wet ARMD causes vision loss due blood and protein leakage below the macula. In certain instances, bleeding, leaking, and scarring from these blood vessels cause irreversible damage to the photoreceptors and rapid vision loss if left untreated.

As used herein, "diabetic proliferative retinopathy" means a disorder of an eye characterized by incompetence of the vascular walls. In certain instances, the lack of oxygen in the retina results in angiogenesis along the retina and in the vitreous humour. In certain instances, the new blood vessels bleed, cloud vision, and destroy the retina.

In certain instances, the proliferation of capillaries supplies a tumor with nutrients, allowing the tumor to expand. In certain instances, the proliferation of capillaries enables the rapid removal of cellular waste enabling tumor growth. In certain instances, angiogenesis facilitates metastasis. In certain instances, the proliferation of capillaries increases the chances that a cancerous cell will be able to enter a blood vessel and thus establish a new tumor at a new site.

Exemplary cancer types that can be treated using an HC•HA complex described herein (e.g., nHC•HA and/or rcHC•HA) include but are not limited to Acute Lymphoblastic Leukemia, Acute Myeloid Leukemia, Adrenocortical Carcinoma, AIDS-Related Cancers, AIDS-Related Lymphoma, Anal Cancer, Astrocytoma, Basal Cell Carcinoma, Bile Duct Cancer, Bladder Cancer, Bladder Cancer, Bone Cancer, Brain Stem Glioma, Brain Tumor, Breast Cancer, Bronchial Adenomas, Burkitt's Lymphoma, Carcinoid Tumor, Carcinoma, Central Nervous System Lymphoma, Cerebellar Astrocytoma, Cervical Cancer, Chronic Lymphocytic Leukemia, Chronic Myelogenous Leukemia, Chronic Myeloproliferative Disorders, Colon Cancer, Colorectal Cancer, Cutaneous T-Cell Lymphoma, Endometrial Cancer, Ependymoma, Esophageal Cancer, Extragonadal Germ Cell Tumor, Eye Cancer, Intraocular Melanoma, Eye Cancer, Retinoblastoma, Gallbladder Cancer, Gastrointestinal Carcinoid Tumor, Gastrointestinal Stromal Tumor (GIST), Germ Cell Tumor (Extracranial), Germ Cell Tumor (Extragonadal), Germ Cell Tumor (Ovarian), Gestational Trophoblastic Tumor, Glioma, Hairy Cell Leukemia, Head and Neck Cancer, Hepatocellular (Liver) Cancer, Hodgkin's Lymphoma, Hypopharyngeal Cancer, Hypothalamic and Visual Pathway Glioma, Intraocular Melanoma, Islet Cell Carcinoma (Endocrine Pancreas), Kaposi's Sarcoma, Kidney (Renal Cell) Cancer, Laryngeal Cancer, Leukemia (Acute Lymphoblastic), Leukemia (Acute Myeloid), Leukemia (Chronic Lymphocytic), Leukemia (Chronic Myelogenous), Lip and Oral Cavity Cancer, Liver Cancer, Lung Cancer (Non-Small Cell), Lung Cancer (Small Cell), Lymphoma, (Cutaneous T-Cell), Lymphoma (Non-Hodgkin's), Malignant Fibrous Histiocytoma of Bone/Osteosarcoma, Medulloblastoma, Melanoma, Merkel Cell Carcinoma, Mesothelioma, Metastatic Squamous Neck Cancer with Occult Primary, Multiple Endocrine Neoplasia Syndrome, Multiple Myeloma/Plasma Cell Neoplasm, Mycosis Fungoides, Myelodysplastic Syndromes, Myelodysplastic/Myeloproliferative Diseases, Myelogenous Leukemia, Myeloid Leukemia, Myeloproliferative Disorders, Nasal Cavity and Paranasal Sinus Cancer, Nasopharyngeal Cancer, Neuroblastoma, Oral Cancer, Oropharyngeal Cancer, Osteosarcoma/Malignant Fibrous Histiocytoma of Bone, Ovarian Cancer, Ovarian Epithelial Cancer, Ovarian Germ Cell Tumor, Ovarian Low Malignant Potential Tumor, Pancreatic Cancer, Parathyroid Cancer, Penile Cancer, Pheochromocytoma, Pineoblastoma and Supratentorial Primitive Neuroectodermal Tumors, Pituitary Tumor, Plasma Cell Neoplasm/Multiple Myeloma, Pleuropulmonary Blastoma, Prostate Cancer, Rectal Cancer, Retinoblastoma, Rhabdomyosarcoma, Salivary Gland Cancer, Sarcoma (Kaposi's), Sarcoma (uterine), Sezary Syndrome, Skin Cancer (non-Melanoma), Skin Cancer (Melanoma), Skin Carcinoma (Merkel Cell), Small Intestine Cancer, Soft Tissue Sarcoma, Squamous Cell Carcinoma, Stomach (Gastric) Cancer, T-Cell Lymphoma, Testicular Cancer, Thymoma, Thyroid Cancer, Trophoblastic Tumor, Gestational, Urethral Cancer, Uterine Cancer, Endometrial, Uterine Sarcoma, Vaginal Cancer, Visual Pathway and Hypothalamic Glioma, Vulvar Cancer, Waldenström's Macroglobulinemia, Wilms' Tumor, and the like.

Methods of Production

Methods involving biological techniques are described herein. Such techniques are described in treatises such as Molecular Cloning: A Laboratory Manual, $3^{rd}$ ed., vol. 1-3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 2003 (with periodic updates). Various conventional techniques for culturing animal cells are described in Culture of Animal Cells: A Manual of Basic Technique, $4^{th}$ ed., R. Ian Freshney, Wiley-Liss, Hoboken, N.J., 2000, and Animal Cell Culture Techniques (Springer Lab Manual), M. Clynos, Springer-Verlag, New York, N.Y., 1998. Methods involving protein analysis and purification are also known in the art and are described in Protein Analysis and Purification: Benchtop Techniques, $2^{nd}$ ed., Ian M. Rosenberg, Birkhauser, New York, N.Y., 2004.

Disclosed herein, in certain embodiments, is a method of isolating HC•HA from amniotic material (e.g., amniotic membrane or chorionic membrane) (nHC•HA). Preferably, the amniotic material is human amniotic material. In some embodiments, the amniotic material is human amniotic membrane. In some embodiments, the amniotic material is chorionic membrane.

Disclosed herein, in certain embodiments, is a method of reconstituting an HC•HA complex (rcHC•HA). In some embodiments, the method comprises contacting (a) hyaluronan (HA); (b) heavy chains of IαI (e.g., HC1 and HC2); and (c) TSG-6, recombinant TSG-6, TSG-6 like protein, recombinant TSG-6 like protein, or combinations thereof.

Disclosed herein, in certain embodiments, is a method of manufacturing an HC•HA complex. In some embodiments, the method comprises contacting (a) hyaluronan (HA); (b) heavy chains of IαI (e.g., HC1 and HC2); and (c) TSG-6, recombinant TSG-6, TSG-6 like protein, recombinant TSG-6 like protein, or combinations thereof; wherein one or more components is generated by a plurality of live cells.

A. Isolation and Purification of nHC•HA

Disclosed herein, in certain embodiments, is a method of isolating HC•HA from amniotic material (e.g., amniotic membrane or chorionic membrane) (nHC•HA). Preferably, the amniotic material is human amniotic material. In some embodiments, the amniotic material is human amniotic membrane. In some embodiments, the amniotic material is human chorionic membrane.

Figure 12:
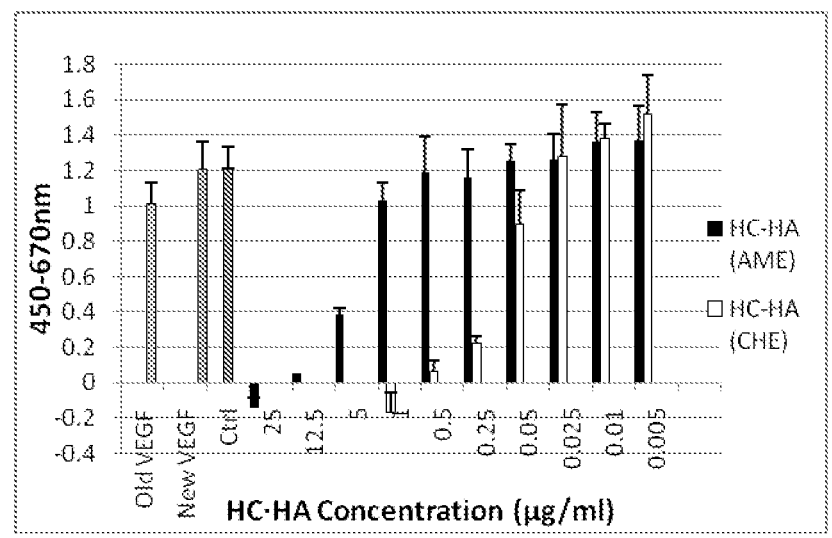
FIG. 12. BrdU ELISA results (A450-670 nm) for HC•HA (AME) and HC•HA(CHE). BrdU ELISA shows adequate difference between labeled control and background control (1.9 vs. 0.65). HC•HA (AME) significantly inhibits proliferation (p<0.05) at 5, 12.5 and 25 μg/ml. HC•HA (CHE) significantly inhibits proliferation (p<0.05) at 0.25, 0.5 and 1 μg/ml. The lowest effective dose for HC•HA (AME) and HC•HA (CHE) is between 1-5 µg/ml and 0.05-0.25 µg/ml respectively. In Aim2b of P-184, the lowest effective dose for HC•HA (ASE) is between 0.2-1 µg/ml (on fibronectin+collagen without VEGF). No statistical difference was found between the VEGF groups (old or new) and the control although a slight lower absorbance value is obtained for the old VEGF compared to control.
Figure 13:
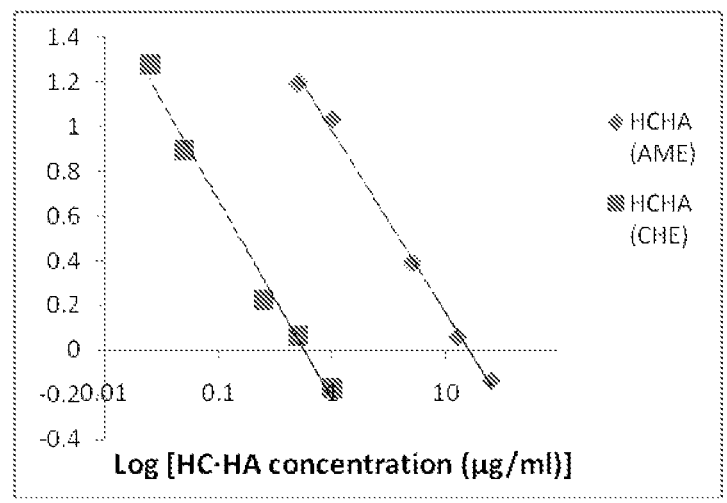
FIG. 13. BrdU ELISA logarithmic plot for HC•HA(AME) and HC•HA(CHE). The absorbance values plotted against HC•HA (AME) and HC•HA (CHE) concentration from 0.5-25 µg/ml fits logarithmic curve equations: $y=-0.35 \ln(x)+0.98$, $R^2=1$ and $y=-0.39 \ln(x)-0.22$, $R^2=0.99$ respectively. The derivatives of the functions for HC•HA (AME) and HC•HA (CHE) are $0.35/[HA]$ and $0.39/[HA]$ respectively.

In some embodiments, nHC•HA isolated from chorionic membrane. In some embodiments, nHC•HA complex purified from chorionic membrane contains a higher protein:HA ratio than nHC•HA isolated from AM (see Table 3 in Example 12). In some embodiments, nHC•HA isolated from chorionic membrane exerts stronger anti-inflammatory and anti-angiogenic activity than nHC•HA isolated from amniotic membrane. In some embodiments, nHC•HA isolated from chorionic membrane is 10-fold more effective as an anti-inflammatory and anti-angiogenic activity than nHC•HA isolated from amniotic membrane. In some embodiments, nHC•HA isolated from chorionic membrane is 15-fold more effective as an anti-inflammatory and anti-angiogenic activity than nHC•HA isolated from amniotic membrane. In some embodiments, nHC•HA isolated from chorionic membrane is 20-fold more effective as an anti-inflammatory and anti-angiogenic activity than nHC•HA isolated from amniotic membrane. In some embodiments, nHC•HA isolated from chorionic membrane is 25-fold more effective as an anti-inflammatory and anti-angiogenic activity than nHC•HA isolated from amniotic membrane. For experimental data showing increased efficacy see FIGS. 12 and 13 and Example 13.

In some embodiments, amniotic material (e.g. powdered amniotic membrane or powdered chorionic membrane) is processed such that it is suitable for nHC•HA complex extraction. In some embodiments, nHC•HA is purified from the processed amniotic material by any suitable method. In some embodiments, the nHC•HA complex is purified by chromatography (e.g., ion exchange, affinity, size exclusion, and hydroxyapatite chromatography), gel filtration, centrifugation (e.g., gradient centrifugation), or differential solubility, ethanol precipitation or by any other available technique for the purification of proteins (See, e.g., Scopes, Protein Purification Principles and Practice 2nd Edition, Springer-Verlag, New York, 1987; Higgins, S. J. and Hames, B. D. (eds.), Protein Expression: A Practical Approach, Oxford Univ Press, 1999; and Deutscher, M. P., Simon, M. I., Abelson, J. N. (eds.), Guide to Protein Purification: Methods in Enzymology (Methods in Enzymology Series, Vol 182), Academic Press, 1997, all incorporated herein by reference).

In some embodiments, the nHC•HA complex is purified by any suitable method or combination of methods. The embodiments described below are not intended to be exclusive, only exemplary.

In some embodiments, the nHC•HA complex is purified by immunoaffinity chromatography. In some embodiments, anti HC1 antibodies, anti-HC2 antibodies, or both are generated and affixed to a stationary support. In some embodiments, the unpurified nHC•HA complex (i.e., the mobile phase) is passed over the support. In certain instances, the nHC•HA complex binds to the antibodies (e.g., via interaction of (a) an HC1 antibody and HC1, (b) an HC2 antibody and HC2, or (c) both). In some embodiments the support is washed (e.g., with PBS) to remove any unbound or loosely bound molecules. In some embodiments, the support is then washed with a solution that enables elution of the nHC•HA complex from the support (e.g., 1% SDS, 6M guanidine-HCl, or 8M urea).

In some embodiments, the nHC•HA complex is purified by affinity chromatography. In some embodiments, HABP is generated and affixed to a stationary support. In some embodiments, the unpurified nHC•HA complex (i.e., the mobile phase) is passed over the support. In certain instances, the nHC•HA complex binds to the HABP. In some embodiments the support is washed (e.g., with PBS) to remove any unbound or loosely bound molecules. In some embodiments, the support is then washed with a solution that enables elution of the nHC•HA complex from the support.

In some embodiments, the nHC•HA complex is purified by a combination of HABP affinity chromatography, and immunoaffinity chromatography using anti HC1 antibodies, anti-HC2 antibodies, or both.

By way of non-limiting example: Amniotic Membrane (AM) powder is mixed with the cold PBS buffer without protease inhibitors at 1:1 (g/ml). The mixture is centrifuged at 48,000×g 4° C. for 30 min. The supernatant (Extract P) is dissolved in CsCl/4M guanidine HCl mixture at the initial density of 1.35 g/ml, and centrifuged at 125,000×g for 48 h at 15° C. The supernatant is extracted and dialyzed against distilled water to remove CsCl and guanidine HCl. The dialysate is mixed with 3 volumes of 95% (v/v) ethanol containing 1.3% (w/v) potassium acetate at 0° C. for 1 h. After centrifugation at 15,000×g, the pellet is washed with 70% (v/v) ethanol and centrifugation. The pellet is briefly dried by air, stored at −80° C.

By way of non-limiting example: Amniotic Membrane (AM) powder is mixed with the cold PBS buffer without protease inhibitors at 1:1 (g/ml). The mixture is centrifuged at 48,000×g 4° C. for 30 min. The supernatant (Extract P) is dissolved in CsCl/4M guanidine HCl mixture at the initial density of 1.35 g/ml, and centrifuged at 125,000×g for 48 h at 15° C. A total of 15 fractions (0.8 ml/fraction) are collected from the top to the bottom of each tube. Besides the density, the concentration of proteins and HA in each fraction is measured by BCA Protein Assay and HA Quantitative Test Kit, respectively. Fractions #8-15, which contain HA but no detectable proteins, are pooled, adjusted with CsCl/4M guanidine HCl at the initial density of 1.40 g/ml, centrifuged, and fractionated in the same manner as described above. Fractions #3-15, which contained HA but no detectable proteins, are pooled and dialyzed against distilled water to remove CsCl and guanidine HCl. The dialysate is mixed with 3 volumes of 95% (v/v) ethanol containing 1.3% (w/v) potassium acetate at 0° C. for 1 h. After centrifugation at 15,000×g, the pellet is washed with 70% (v/v) ethanol and centrifugation. The pellet is briefly dried by air, stored at −80° C.

By way of non-limiting example: Chorionic Membrane (CH) powder is mixed with the cold PBS buffer without protease inhibitors at 1:1 (g/ml). The mixture is centrifuged at 48,000×g 4° C. for 30 min. The supernatant (Extract P) is dissolved in CsCl/4M guanidine HCl mixture at the initial density of 1.35 g/ml, and centrifuged at 125,000×g for 48 h at 15° C. The supernatant is extracted and dialyzed against distilled water to remove CsCl and guanidine HCl. The dialysate is mixed with 3 volumes of 95% (v/v) ethanol containing 1.3% (w/v) potassium acetate at 0° C. for 1 h. After centrifugation at 15,000×g, the pellet is washed with 70% (v/v) ethanol and centrifugation. The pellet is briefly dried by air, stored at −80° C.

B. Bioreactor Production of an rcHC•HA Complex without Use of Live Cells

Disclosed herein, in certain embodiments, is a method of reconstituting an rcHC•HA complex. In some embodiments, the method comprises contacting (a) hyaluronan (HA); (b) heavy chains of IαI (e.g., HC1 and HC2); and (c) TSG-6, recombinant TSG-6, TSG-6 like protein, recombinant TSG-6 like protein, or combinations thereof.

In some embodiments, heavy chains of IαI are isolated from serum. In some embodiments, heavy chains of IαI are not isolated from serum. In some embodiments, heavy chains of IαI are prepared by recombinant technology.

In some embodiments, TSG6 or TSG-6 like protein is isolated from a cell or a plurality of cells (e.g., a tissue extract). In some embodiments, TSG6 or TSG-6 like protein is not isolated from a cell or a plurality of cells (e.g., a tissue extract). In some embodiments, TSG6 or TSG-6 like protein is prepared by recombinant technology.

In some embodiments, HA (e.g., HMW HA) is contacted with HC1 and HC2 of IαI (e.g., from unpurified serum, purified from serum, or recombinant peptides); and TSG-6. In some embodiments, HA (e.g., HMW HA) is contacted with HC1 and HC2 of IαI (e.g., from unpurified serum, purified from serum, or recombinant peptides); and recombinant TSG-6 (e.g., TSG-6Q). In some embodiments, HA (e.g., HMW HA) is contacted with HC1 and HC2 of IαI (e.g., from unpurified serum, purified from serum, or recombinant peptides); and TSG-6 like protein. In some embodiments, HA (e.g., HMW HA) is contacted with (a) heavy chains of IαI (e.g., HC1 and HC2; from unpurified serum, purified from serum, or recombinant peptides); and (b) TSG-6, recombinant TSG-6, TSG-6 like protein, recombinant TSG-6 like protein, or combinations thereof. In some embodiments, the contacting occurs for at least 6 hours, at least 12 hours, at least 24 hours, at least 36 hours, at least 48 hours, at least 60 hours, or at least 72 hours.

In some embodiments, the method further comprises HA binding protein (HABP). In some embodiments, HABP is affixed to a stationary support (e.g., by cross-linking). In some embodiments, the stationary support comprising HABP is contacted with HA (e.g., HMW HA), a heavy chain of IαI and a rcHC•HA catalytic protein selected from TSG-6, recombinant TSG-6, TSG-6 like protein, recombinant TSG-6 like protein, or combinations thereof. In some embodiments, the contacting occurs for at least 6 hours, at least 12 hours, at least 24 hours, at least 36 hours, at least 48 hours, at least 60 hours, or at least 72 hours. In some embodiments, the stationary support is washed to remove any unbound components.

In some embodiments, the rcHC•HA complex is purified by any suitable method or combination of methods. The embodiments described below are not intended to be exclusive, only exemplary.

In some embodiments, the rcHC•HA complex is purified by chromatography (e.g., ion exchange, affinity, size exclusion, and hydroxyapatite chromatography), gel filtration, centrifugation (e.g., gradient centrifugation), or differential solubility, ethanol precipitation or by any other available technique for the purification of proteins (See, e.g., Scopes, Protein Purification Principles and Practice 2nd Edition, Springer-Verlag, New York, 1987; Higgins, S. J. and Hames, B. D. (eds.), Protein Expression: A Practical Approach, Oxford Univ Press, 1999; and Deutscher, M. P., Simon, M. I., Abelson, J. N. (eds.), Guide to Protein Purification: Methods in Enzymology (Methods in Enzymology Series, Vol 182), Academic Press, 1997, all incorporated herein by reference).

In some embodiments, the rcHC•HA complex is purified by immunoaffinity chromatography. In some embodiments, anti HC1 antibodies, anti-HC2 antibodies, or both are generated and affixed to a stationary support. In some embodiments, the unpurified rcHC•HA complex (i.e., the mobile phase) is passed over the support. In certain instances, the rcHC•HA complex binds to the antibodies (e.g., via interaction of (a) an HC1 antibody and HC1, (b) an HC2 antibody and HC2, or (c) both). In some embodiments the support is washed (e.g., with PBS) to remove any unbound or loosely bound molecules. In some embodiments, the support is then washed with a solution that enables elution of the rcHC•HA complex from the support (e.g., 1% SDS, 6M guanidine-HCl, or 8M urea).

In some embodiments, the rcHC•HA complex is purified by affinity chromatography. In some embodiments, HABP is generated and affixed to a stationary support. In some embodiments, the unpurified rcHC•HA complex (i.e., the mobile phase) is passed over the support. In certain instances, the rcHC•HA complex binds to the HABP. In some embodiments the support is washed (e.g., with PBS) to remove any unbound or loosely bound molecules. In some embodiments, the support is then washed with a solution that enables elution of the rcHC•HA complex from the support.

In some embodiments, the rcHC•HA complex is purified by a combination of HABP affinity chromatography, and immunoaffinity chromatography using anti HC1 antibodies, anti-HC2 antibodies, or both.

C. Bioreactor Production of an rcHC•HA Complex via Use of Live Cells

Disclosed herein, in certain embodiments, is a method of reconstituting an rcHC•HA complex via use of live cells. In some embodiments, the method comprises contacting (a) hyaluronan (HA); (b) a heavy chain of IαI (e.g., HC1 and HC2); and (c) TSG-6, TSG-6 like protein, or combinations thereof; wherein one or more components is generated or expressed by a plurality of cells in a bioreactor.

In some embodiments, the method comprises HA that is obtained from a commercial supplier. In some embodiments, the method comprises HA that is generated by a plurality of cells in a bioreactor. In some embodiments, the plurality of cells constitutively generate HA. In some embodiments, the plurality of cells constitutively expresses HAS1, HAS2, HAS3, or a combination thereof. In some embodiments, the plurality of cells are contacted with at least one factor known to upregulate HAS1, HAS2, HAS3, or a combination thereof.

In some embodiments, the method comprises a heavy chain of IαI is isolated from serum. In some embodiments, the method comprises a heavy chain of IαI that is not isolated from serum. In some embodiments, the method comprises a heavy chain of IαI that is expressed by a plurality of cells in a bioreactor. In some embodiments, the method comprises HC1 that is expressed by a plurality of cells in a bioreactor. In some embodiments, the method comprises HC2 that is expressed by a plurality of cells in a bioreactor. In some embodiments, the plurality of cells constitutively expresses a heavy chain of IαI. In some embodiments, the plurality of cells constitutively expresses constitutively express HC1. In some embodiments, the plurality of cells constitutively expresses HC2.

In some embodiments, the method comprises TSG-6 or TSG-6 like protein that is isolated from a cell or a plurality of cells (e.g., a tissue extract). In some embodiments, the method comprises TSG-6 or TSG-6 like protein that is not isolated from a cell or a plurality of cells (e.g., a tissue extract). In some embodiments, the method comprises TSG-6 or TSG-6 like protein that is expressed by a plurality of cells in a bioreactor. In some embodiments, the plurality of cells constitutively generates TSG-6 or TSG-6 like protein. In some embodiments, the plurality of cells constitutively expresses TSG-6 or TSG-6 like protein. In some embodiments, the plurality of cells is contacted with at least one factor known to upregulate TSG-6 or TSG-6 like protein.

Constitutive Expression

In some embodiments, a cell that constitutively (a) expresses a heavy chain of IαI (e.g., HC1 and HC2); or (b) express TSG-6, TSG-6 like protein is generated by any suitable method. In some embodiments, a cell that constitutively (a) expresses a heavy chain of IαI (e.g., HC1 and HC2); or (b) express TSG-6, TSG-6 like protein is generated by introducing point mutations into the gene encoding (a) a heavy chain of IαI (e.g., HC1 and HC2); or (b) TSG-6, TSG-6 like protein. In some embodiments, the mutations are substitution mutations, deletion mutations, or insertion mutations.

In some embodiments, a cell that constitutively generates HA is produced by any suitable method. In some embodiments, a cell that constitutively generates HA is produced by introducing point mutations into a gene encoding HAS1, HAS2, HAS3, or a combination thereof. In some embodiments, the mutations are substitution mutations, deletion mutations, or insertion mutations. In some embodiments, a cell that constitutively generates HA is produced by contacting the cell with at least one factor known to upregulate HAS1, HAS2, HAS3, or a combination thereof.

Generation of Cell Lines

In some embodiments, the plurality of cells comprises mammalian cells. In some embodiments, the plurality of cells comprises Chinese Hamster ovary-derived CHO cells; human HeLa cells; HEK293 cells; amniotic epithelial cell; amniotic stromal mesenchymal cells; or combinations thereof. In some embodiments, a gene sequence of interest is cloned into a suitable expression vector which is then inserted into a host cell. In some embodiments, the vector is pMSG, or pcDNA3.1(+). In some embodiments, the host cell is transformed with the vector by use of calcium phosphate method, DEAE-dextran method, lipofection, or electroporation. In some embodiments, a gene sequence of interest is cloned into a suitable expression vector which then inserts into the genome of the cells. In some embodiments, the vector is a retrovirus, lentivirus, an adenovirus, or a combination thereof.

In some embodiments, the plurality of cells comprises bacterial cells (e.g., *E. coli*). In some embodiments, a gene sequence of interest is cloned into a suitable expression vector which is then inserted into a host cell. In some embodiments, the host is a bacterial cell. In some embodiments, the vector is pET-3 or pGEX-1. In some embodiments, the host cell is transformed with the vector by electroporation or the Hanahan method. In some embodiments, a gene sequence of interest is cloned into a suitable expression vector which then inserts into the genome of the cells. In some embodiments, the vector is a retrovirus, lentivirus, an adenovirus, or a combination thereof.

In some embodiments, the plurality of cells comprises yeast cells. In some embodiments, a gene sequence of interest is cloned into a suitable expression vectors which is then inserted into a host cell. In some embodiments, the host cell is transformed with the vector by spheroplast fusion or lithium acetate methods. In some embodiments, a gene sequence of interest is cloned into a suitable expression vector which then inserts into the genome of the cells. In some embodiments, the vector is a retrovirus, lentivirus, an adenovirus, or a combination thereof In some embodiments, the method further comprises confirming expression of the gene sequence of interest. In some embodiments, any suitable method is used. In some embodiments, immunohistochemistry, immunoprecipitation, flow cytometry, immunofluorescence microscopy, SDS-PAGE, Western blots, enzyme-linked immunosorbentassay (ELISA), high performance liquid chromatography (HPLC) techniques, biological activity assays or affinity chromatography is used.

Starter Cultures

In some embodiments, a plurality of cells described above is cultured by any suitable method.

In some embodiments, the cells are first expanded in a starter culture (e.g., 1 10 mL culture, overnight). In some embodiments, the cells are grown in Ham's F10 (Sigma), Basal medium (BEM), Minimal Essential Medium (MEM), RPMI-1640, Supplemental Hormone Medium (SHEM), or Dulbecco's Modified Eagle's Medium (DMEM). In some embodiments, a cell culture further comprises serum (e.g., fetal calf sera, newborn calf sera, human sera, equine sera). In some embodiments, a cell culture is agitated to increase oxygenation of the medium and dispersion of nutrients to the cells.

In some embodiments, the cells are passaged several times in bioreactors of increasing volume before the cells are placed in the production bioreactor. In some embodiments, the cells are passaged to the succeeding bioreactor while still in contact with the media in which the cells were previously grown. In some embodiments, the cells are removed from the media, for example, by low-speed centrifugation before being passaged to the succeeding bioreactor. In some embodiments, the cells are washed with fresh with media before seeding the next bioreactor to remove any unwanted metabolic waste products or medium components. In some embodiments, the media is the same in each bioreactor. In some embodiments, the media varies between bioreactors.

In some embodiments, the expanded cells from one bioreactor are diluted before being added to the succeeding bioreactor. In some embodiments, the starting cell density for the production bioreactor is from about $2 \times 10^2$ viable cells per mL to about $2 \times 10^3$, $2 \times 10^4$, $2 \times 10^5$, $2 \times 10^6$, $5 \times 10^6$ or $10 \times 10^6$ viable cells per mL and higher.

Production Bioreactor

In some embodiments, a cell culture is maintained in the initial growth phase under conditions conducive to the survival, growth and viability of the cell culture. The necessary environmental conditions will vary depending on the cell type, the organism from which the cell was derived, and the nature and character of the expressed polypeptides, HA, and the rcHC•HA complex.

In some embodiments, the temperature of the cell culture in the initial growth phase will be selected based primarily on the range of temperatures at which the cell culture remains viable. For example, during the initial growth phase, CHO cells grow well at 37° C. In some embodiments, the temperature is from about 25° C. to about 42° C. In some embodiments, the temperature is from about 35° C. to 40° C.

In some embodiments, the temperature of the initial growth phase is maintained at a single, constant temperature. In some embodiments, the temperature of the initial growth phase is maintained within a range of temperatures. In some embodiments, the temperature is increased or decreased during the initial growth phase. In some embodiments, the temperature is steadily increased or decreased during the initial growth phase. In some embodiments, the temperature is increased or decreased by discrete amounts at various times during the initial growth phase.

In some embodiments, the cells are grown for a period of time sufficient to achieve a viable cell density that is a given percentage of the maximal viable cell density that the cells would eventually reach if allowed to grow undisturbed. In some embodiments, the cells are grown for a period of time sufficient to achieve a desired viable cell density of 1, 5, 10, 15, 20, 25, 30, 35, 40, 45, 50, 55, 60, 65, 70, 75, 80, 85, 90, 95 or 99 percent of maximal viable cell density.

In some embodiments, the cells are grown for a defined period of time regardless of their density. In some embodiments, the cells are grown for 0, 1, 2, 3, 4, 5, 6, 7, 8, 9, 10, 11, 12, 13, 14, 15, 16, 17, 18, 19, 20 or more days. In some embodiments, the cells are grown for a month.

In some embodiments, the cell culture is agitated during the initial culture phase in order to increase oxygenation and dispersion of nutrients to the cells.

Shifting Culture Conditions

Following achievement of the desired cell density (or the end of the prescribed growth time), in some embodiments at least one of the culture conditions is shifted. In some embodiments, the culture conditions are shifted by shifting the temperature of the culture. In some embodiments, the culture conditions are shifted by shifting the osmolarity of the culture. On the other hand, in some embodiments, the culture conditions are prevented from shifting to undesired conditions, e.g., by keeping the pH of the culture condition at or around neutral conditions, and if necessary to prevent a shift to an alkaline pH (which has the potential to break the covalent bonds between HA and HC).

In some embodiments, the condition shift is gradual. In some embodiments, the condition shift occurs over several hours. In some embodiments, the condition shift occurs over about 24 hours. In some embodiments, the condition shift occurs over several days. In some embodiments, the condition sh Dosage Forms In some embodiments, an HC•HA complex disclosed herein (e.g., nHC•HA and/or rcHC•HA) is administered as an aqueous suspension. In some embodiments, an aqueous suspension comprises a sweetening or flavoring agent, coloring matters or dyes and, if desired, emulsifying agents or suspending agents, together with diluents water, ethanol, propylene glycol, glycerin, or combinations thereof. In some embodiments, an aqueous suspension comprises a suspending agent. In some embodiments, an aqueous suspension comprises sodium carboxymethylcellulose, methylcellulose, hydroxypropylmethyl-cellulose, sodium alginate, polyvinylpyrrolidone, gum tragacanth and/or gum acacia. In some embodiments, an aqueous suspension comprises a dispersing or wetting agent. In some embodiments, an aqueous suspension comprises a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. In some embodiments, an aqueous suspension comprises a preservative. In some embodiments, an aqueous suspension comprises ethyl, or n-propyl p-hydroxybenzoate. In some embodiments, an aqueous suspension comprises a sweetening agent. In some embodiments, an aqueous suspension comprises sucrose, saccharin or aspartame.

In some embodiments, an HC•HA complex disclosed herein (e.g., nHC•HA and/or rcHC•HA) is administered as an oily suspension. In some embodiments, an oily suspension is formulated by suspending the active ingredient in a vegetable oil (e.g., arachis oil, olive oil, sesame oil or coconut oil), or in mineral oil (e.g., liquid paraffin). In some embodiments, an oily suspension comprises a thickening agent (e.g., beeswax, hard paraffin or cetyl alcohol). In some embodiments, an oily suspension comprises sweetening agents (e.g., those set forth above). In some embodiments, an oily suspension comprises an anti-oxidant (e.g., butylated hydroxyanisol or alpha-tocopherol).

In some embodiments, an HC•HA complex (e.g., nHC•HA and/or rcHC•HA) disclosed herein is formulated for parenteral injection (e.g., via injection or infusion, including intraarterial, intracardiac, intradermal, intraduodenal, intramedullary, intramuscular, intraosseous, intraperitoneal, intrathecal, intravascular, intravenous, intravitreal, epidural and/or subcutaneous). In some embodiments, an HC•HA complex disclosed herein (e.g., nHC•HA and/or rcHC•HA) is administered as a sterile solution, suspension or emulsion.

In some embodiments, a formulation for parenteral administration includes aqueous and/or non-aqueous (oily) sterile injection solutions of an HC•HA complex disclosed herein (e.g., nHC•HA and/or rcHC•HA) which may contain antioxidants, buffers, bacteriostats and/or solutes which render the formulation isotonic with the blood of the intended recipient; and/or aqueous and/or non-aqueous sterile suspensions which may include a suspending agent and/or a thickening agent. In some embodiments, a formulation for parenteral administration includes suitable stabilizers or agents which increase the solubility of an HC•HA complex disclosed herein (e.g., nHC•HA and/or rcHC•HA) to allow for the preparation of highly concentrated solutions.

In some embodiments, an HC•HA complex disclosed herein (e.g., nHC•HA and/or rcHC•HA) is administered as an aqueous suspension. In some embodiments, an aqueous suspension comprises water, Ringer's solution and/or isotonic sodium chloride solution.

In some embodiments, an HC•HA complex disclosed herein (e.g., nHC•HA and/or rcHC•HA) is administered as an oil-in-water micro-emulsion where the active ingredient is dissolved in the oily phase. In some embodiments, an HC•HA complex disclosed herein (e.g., nHC•HA and/or rcHC•HA) is dissolved in a fatty oil (e.g., sesame oil, or synthetic fatty acid esters, (e.g., ethyl oleate or triglycerides, or liposomes. In some embodiments, an HC•HA complex disclosed herein (e.g., nHC•HA and/or rcHC•HA) is dissolved in a mixture of soybean oil and/or lecithin. In some embodiments, the oil solution is introduced into a water and glycerol mixture and processed to form a micro-emulsion.

In some embodiments, a composition formulated for parenteral administration is administered as a single bolus shot. In some embodiments, a composition formulated for parenteral administration is administered via a continuous intravenous delivery device (e.g., Deltec CADD-PLUS™ model 5400 intravenous pump).

In some embodiments, a formulation for injection is presented in unit dosage form, e.g., in ampoules or in multi-dose containers, with an added preservative. In some embodiments, a formulation for injection is stored in powder form or in a freeze-dried (lyophilized) condition requiring only the addition of the sterile liquid carrier, for example, saline or sterile pyrogen-free water, immediately prior to use.

In some embodiments, an HC•HA complex (e.g., nHC•HA and/or rcHC•HA) disclosed herein is formulated for topical administration. Topical formulations include, but are not limited to, ointments, creams, lotions, solutions, pastes, gels, sticks, liposomes, nanoparticles. In some embodiments, a topical formulation is administered by use of a patch, bandage or wound dressing.

In some embodiments, a topical formulation comprises a gelling (or thickening) agent. Suitable gelling agents include, but are not limited to, celluloses, cellulose derivatives, cellulose ethers (e.g., carboxymethylcellulose, ethylcellulose, hydroxyethylcellulose, hydroxymethylcellulose, hydroxypropylmethylcellulose, hydroxypropylcellulose, methylcellulose), guar gum, xanthan gum, locust bean gum, alginates (e.g., alginic acid), silicates, starch, tragacanth, carboxyvinyl polymers, carrageenan, paraffin, petrolatum, acacia (gum arabic), agar, aluminum magnesium silicate, sodium alginate, sodium stearate, bladderwrack, bentonite, carbomer, carrageenan, carbopol, xanthan, cellulose, microcrystalline cellulose (MCC), ceratonia, chondrus, dextrose, furcellaran, gelatin, ghatti gum, guar gum, hectorite, lactose, sucrose, maltodextrin, mannitol, sorbitol, honey, maize starch, wheat starch, rice starch, potato starch, gelatin, sterculia gum, polyethylene glycol (e.g. PEG 200-4500), gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly(methoxyethyl methacrylate), poly(methoxyethoxyethyl methacrylate), hydroxypropyl cellulose, hydroxypropylmethyl-cellulose (HPMC), sodium carboxymethyl-cellulose (CMC), silicon dioxide, polyvinylpyrrolidone (PVP: povidone), or combinations thereof.

In some embodiments, a topical formulation disclosed herein comprises an emollient. Emollients include, but are not limited to, castor oil esters, cocoa butter esters, safflower oil esters, cottonseed oil esters, corn oil esters, olive oil esters, cod liver oil esters, almond oil esters, avocado oil esters, palm oil esters, sesame oil esters, squalene esters, kikui oil esters, soybean oil esters, acetylated monoglycerides, ethoxylated glyceryl monostearate, hexyl laurate, isohexyl laurate, isohexyl palmitate, isopropyl palmitate, methyl palmitate, decyloleate, isodecyl oleate, hexadecyl stearate decyl stearate, isopropyl isostearate, methyl isostearate, diisopropyl adipate, diisohexyl adipate, dihexyldecyl adipate, diisopropyl sebacate, lauryl lactate, myristyl lactate, and cetyl lactate, oleyl myristate, oleyl stearate, and oleyl oleate, pelargonic acid, lauric acid, myristic acid, palmitic acid, stearic acid, isostearic acid, hydroxystearic acid, oleic acid, linoleic acid, ricinoleic acid, arachidic acid, behenic acid, erucic acid, lauryl alcohol, myristyl alcohol, cetyl alcohol, hexadecyl alcohol, stearyl alcohol, isostearyl alcohol, hydroxystearyl alcohol, oleyl alcohol, ricinoleyl alcohol, behenyl alcohol, erucyl alcohol, 2-octyl dodecanyl alcohol, lanolin and lanolin derivatives, beeswax, spermaceti, myristyl myristate, stearyl stearate, carnauba wax, candelilla wax, lecithin, and cholesterol.

In some embodiments, an HC•HA complex (e.g., nHC•HA and/or rcHC•HA) disclosed herein is formulated for administration to an eye or a tissue related thereto. Formulations suitable for administration to an eye include, but are not limited to, solutions, suspensions (e.g., an aqueous suspension), ointments, gels, creams, liposomes, niosomes, pharmacosomes, nanoparticles, or combinations thereof. In some embodiments, an HC•HA complex disclosed herein (e.g., nHC•HA and/or rcHC•HA) for topical administration to an eye is administered spraying, washing, or combinations thereof. In some embodiments, an HC•HA complex disclosed herein (e.g., nHC•HA and/or rcHC•HA) is administered to an eye via an injectable depot preparation.

As used herein, a "depot preparation" is a controlled-release formulation that is implanted in an eye or a tissue related thereto (e.g., the sclera) (for example subcutaneously, intramuscularly, intravitreally, or within the subconjunctiva). In some embodiments, a depot preparation is formulated by forming microencapsulated matrices (also known as microencapsule matrices) of an HC•HA complex disclosed herein (e.g., nHC•HA and/or rcHC•HA) in biodegradable polymers. In some embodiments, a depot preparation is formulated by entrapping an HC•HA complex disclosed herein (e.g., nHC•HA and/or rcHC•HA) in liposomes or microemulsions.

A formulation for administration to an eye has an ophthalmically acceptable tonicity. In certain instances, lacrimal fluid has an isotonicity value equivalent to that of a 0.9% sodium chloride solution. In some embodiments, an isotonicity value from about 0.6% to about 1.8% sodium chloride equivalency is suitable for topical administration to an eye. In some embodiments, a formulation for administration to an eye disclosed herein has an osmolarity from about 200 to about 600 mOsm/L. In some embodiments, a formulation for administration to an eye disclosed herein is hypotonic and thus requires the addition of any suitable to attain the proper tonicity range. Ophthalmically acceptable substances that modulate tonicity include, but are not limited to, sodium chloride, potassium chloride, sodium thiosulfate, sodium bisulfite and ammonium sulfate.

A formulation for administration to an eye has an ophthalmically acceptable clarity. Examples of ophthalmically-acceptable clarifying agents include, but are not limited to, polysorbate 20, polysorbate 80, or combinations thereof.

In some embodiments, a formulation for administration to an eye comprises an ophthalmically acceptable viscosity enhancer. In some embodiments, a viscosity enhancer increases the time a formulation disclosed herein remains in an eye. In some embodiments, increasing the time a formulation disclosed herein remains in the eye allows for greater drug absorption and effect. Non-limiting examples of mucoadhesive polymers include carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, a formulation for administration to an eye is administered or delivered to the posterior segments of an eye (e.g., to the retina, choroid, vitreous and optic nerve). In some embodiments, a topical formulation for administration to an eye disclosed herein for delivery to the posterior of the eye comprises a solubilizing agent, for example, a glucan sulfate and/or a cyclodextrin. Glucan sulfates which can be used include, but are not limited to, dextran sulfate, cyclodextrin sulfate and β-1,3-glucan sulfate, both natural and derivatives thereof, or any compound which can temporarily bind to and be retained at tissues which contain fibroblast growth factor (FGF), which improves the stability and/or solubility of a drug, and/or which improves penetration and ophthalmic absorption of a topical formulation for administration to an eye disclosed herein. Cyclodextrin derivatives that can be used as a solubilizing agent include, but are not limited to, α-cyclodextrin, β-cyclodextrin, γ-cyclodextrin, hydroxyethyl β-cyclodextrin, hydroxypropyl γ-cyclodextrin, hydroxypropyl β-cyclodextrin, sulfated β-cyclodextrin, sulfated α-cyclodextrin, sulfobutyl ether β-cyclodextrin.

In some embodiments, an HC•HA complex (e.g., nHC•HA and/or rcHC•HA) disclosed herein is formulated for rectal or vaginal administration. In some embodiments, an HC•HA complex disclosed herein (e.g., nHC•HA and/or rcHC•HA) is administered as a suppository. In some embodiments, a composition suitable for rectal administration is prepared by mixing an HC•HA complex disclosed herein (e.g., nHC•HA and/or rcHC•HA) with a suitable non-irritating excipient which is solid at ordinary temperatures but liquid at the rectal temperature and will therefore melt in the rectum to release the drug. In some embodiments, a composition suitable for rectal administration is prepared by mixing an HC•HA complex disclosed herein (e.g., nHC•HA and/or rcHC•HA) with cocoa butter, glycerinated gelatin, hydrogenated vegetable oils, mixtures of polyethylene glycols of various molecular weights or fatty acid esters of polyethylene glycol.

Dosages

The amount of pharmaceutical compositions administered will firstly be dependent on the individual being treated. In the instances where pharmaceutical compositions are administered to a human subject, the daily dosage will normally be determined by the prescribing physician with the dosage generally varying according to the age, sex, diet, weight, general health and response of the individual, the severity of the individual's symptoms, the precise indication or condition being treated, the severity of the indication or condition being treated, time of administration, route of administration, the disposition of the composition, rate of excretion, drug combination, and the discretion of the prescribing physician.

In some embodiments, the dosage of an HC•HA complex (e.g., nHC•HA and/or rcHC•HA) is between about 0.001 to about 1000 mg/kg body weight/day. In some embodiments, the amount of HC•HA complex disclosed herein (e.g., nHC•HA and/or rcHC•HA) is in the range of about 0.5 to about 50 mg/kg/day. In some embodiments, the amount of HC•HA complex disclosed herein (e.g., nHC•HA and/or rcHC•HA) is about 0.001 to about 7 g/day. In some embodiments, the amount of HC•HA complex disclosed herein (e.g., nHC•HA and/or rcHC•HA) is about 0.01 to about 7 g/day. In some embodiments, the amount of HC•HA complex disclosed herein (e.g., nHC•HA and/or rcHC•HA) is about 0.02 to about 5 g/day. In some embodiments, the amount of HC•HA complex disclosed herein (e.g., nHC•HA and/or rcHC•HA) is about 0.05 to about 2.5 g/day. In some embodiments, the amount of HC•HA complex disclosed herein (e.g., nHC•HA and/or rcHC•HA) is about 0.1 to about 1 g/day.

An HC•HA complex (e.g., nHC•HA and/or rcHC•HA) disclosed herein and combination therapies can be administered before, during or after the occurrence of a disease or condition, and the timing of administering the composition containing an HC•HA complex disclosed herein (e.g., nHC•HA and/or rcHC•HA) can vary. Thus, for example, an HC•HA complex disclosed herein (e.g., nHC•HA and/or rcHC•HA) is used as a prophylactic and is administered continuously to subjects with a propensity to develop conditions or diseases in order to prevent the occurrence of the disease or condition. An HC•HA complex disclosed herein (e.g., nHC•HA and/or rcHC•HA) can be administered to a subject during or as soon as possible after the onset of the symptoms. The administration of an HC•HA complex disclosed herein (e.g., nHC•HA and/or rcHC•HA) can be initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration can be via any route practical, such as, for example, an intravenous injection, a bolus injection, infusion over 5 minutes to about 5 hours, a pill, a capsule, transdermal patch, buccal delivery, and the like, or combination thereof. An HC•HA complex disclosed herein (e.g., nHC•HA and/or rcHC•HA) is preferably administered as soon as is practicable after the onset of a disease or condition is detected or suspected, and for a length of time necessary for the treatment of the disease, such as, for example, from about 1 month to about 3 months. The length of treatment can vary for each subject, and the length can be determined using the known criteria. For example, an HC•HA complex disclosed herein (e.g., nHC•HA and/or rcHC•HA) or a formulation containing a complex can be administered for at least 2 weeks, preferably about 1 month to about 5 years, and more preferably from about 1 month to about 3 years.

In some embodiments, an HC•HA complex (e.g., nHC•HA and/or rcHC•HA) disclosed herein is administered in a single dose, once daily. In some embodiments, an HC•HA complex disclosed herein (e.g., nHC•HA and/or rcHC•HA) is administered in multiple doses, more than once per day. In some embodiments an HC•HA complex disclosed herein (e.g., nHC•HA and/or rcHC•HA) is administered twice daily. In some embodiments, an HC•HA complex disclosed herein (e.g., nHC•HA and/or rcHC•HA) is administered three times per day. In some embodiments, an HC•HA complex is administered four times per day. In some embodiments, an HC•HA complex disclosed herein (e.g., nHC•HA and/or rcHC•HA) is administered more than four times per day.

In some embodiments, an HC•HA complex disclosed herein (e.g., nHC•HA and/or rcHC•HA) is administered for prophylactic and/or therapeutic treatments. In therapeutic applications, an HC•HA complex disclosed herein (e.g., nHC•HA and/or rcHC•HA) is administered to an individual already suffering from a disease or condition, in an amount sufficient to cure or at least partially arrest the symptoms of the disease or condition. Amounts effective for this use will depend on the severity and course of the disease or condition, previous therapy, the individual's health status, weight, and response to the drugs, and the judgment of the treating physician.

In prophylactic applications, an HC•HA complex disclosed herein (e.g., nHC•HA and/or rcHC•HA) is administered to an individual that is at risk of a particular disorder. Such an amount is defined to be a "prophylactically effective amount or dose." In this use, the precise amounts also depend on the individual's state of health, weight, and the like.

In the case wherein the individual's condition does not improve, upon the doctor's discretion an HC•HA complex disclosed herein (e.g., nHC•HA and/or rcHC•HA) is administered chronically, that is, for an extended period of time, including throughout the duration of the individual's life in order to ameliorate or otherwise control or limit the symptoms of the individual's disease or condition.

In the case wherein the individual's status does improve, upon the doctor's discretion an HC•HA complex disclosed herein (e.g., nHC•HA and/or rcHC•HA) is administered continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the individual's conditions has occurred, a maintenance dose is administered if necessary. Subsequently, the dosage or the frequency of administration, or both, can be reduced, as a function of the symptoms, to a level at which the improved disease, disorder or condition is retained. Individuals can, however, require intermittent treatment on a long-term basis upon any recurrence of symptoms.

The pharmaceutical composition described herein may be in unit dosage forms suitable for single administration of precise dosages. In unit dosage form, the formulation is divided into unit doses containing appropriate quantities of an HC•HA complex disclosed herein (e.g., nHC•HA and/or rcHC•HA). The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi dose containers, with an added preservative.

The daily dosages appropriate for an HC•HA complex disclosed herein (e.g., nHC•HA and/or rcHC•HA) are from about 0.01 to 2.5 mg/kg per body weight. An indicated daily dosage in the larger mammal, including, but not limited to, humans, is in the range from about 0.5 mg to about 100 mg, conveniently administered in divided doses, including, but not limited to, up to four times a day or in extended release form. Suitable unit dosage forms for oral administration include from about 1 to 50 mg active ingredient. The foregoing ranges are merely suggestive, as the number of variables in regard to an individual treatment regime is large, and considerable excursions from these recommended values are not uncommon. Such dosages may be altered depending on a number of variables, not limited to the activity of an HC•HA complex used (e.g., nHC•HA and/or rcHC•HA), the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. HC•HA complexes exhibiting high therapeutic indices are preferred. The data obtained from cell culture assays and animal studies can be used in formulating a range of dosage for use in human. The dosage of an HC•HA complex disclosed herein (e.g., nHC•HA and/or rcHC•HA) lies preferably within a range of circulating concentrations that include the $ED_{50}$ with minimal toxicity. The dosage may vary within this range depending upon the dosage form employed and the route of administration utilized.

VI. Combinations

In some embodiments, the compositions and methods described herein are used in conjunction with a second therapeutic agent. In some embodiments, an HC•HA complex disclosed herein (e.g., nHC•HA and/or rcHC•HA) and a second therapeutic agent are administered in the same dosage form. In some embodiments, an HC•HA complex disclosed herein (e.g., nHC•HA and/or rcHC•HA) and a second therapeutic agent are administered in separate dosage forms.

In some embodiments, an HC•HA complex disclosed herein (e.g., nHC•HA and/or rcHC•HA) and a second therapeutic agent are administered concurrently (e.g., simultaneously, essentially simultaneously or within the same treatment protocol).

In some embodiments, an HC•HA complex disclosed herein (e.g., nHC•HA and/or rcHC•HA) and a second therapeutic agent are administered sequentially. In some embodiments, an HC•HA complex disclosed herein (e.g., nHC•HA and/or rcHC•HA) is administered before or after the second therapeutic agent. In some embodiments, the time period between administration of an HC•HA complex disclosed herein (e.g., nHC•HA and/or rcHC•HA) and a second active agent ranges from a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval. In some embodiments, the timing between the administration of an HC•HA complex disclosed herein (e.g., nHC•HA and/or rcHC•HA) and a second active agent is about less than an hour, less than a day, less than a week, or less than a month.

In some embodiments, the co-administration of an HC•HA complex disclosed herein (e.g., nHC•HA and/or rcHC•HA) results in an HC•HA complex's requiring a lower dosage than is required when administering an HC•HA complex alone. In some embodiments, the co-administration of a second therapeutic agent results in the second agent's requiring a lower dosage than is required when administering the second agent alone. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature. Combination treatment further includes periodic treatments that start and stop at various times to assist with the clinical management of the individual.

In some embodiments, the second therapeutic agent is selected from cytotoxic agents, anti-angiogenesis agents and/or anti-neoplastic agents. In some embodiments, the second therapeutic agent is selected from alkylating agents, antimetabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, haematopoietic growth factors, aromatase inhibitors, anti-estrogens, anti-androgens, corticosteroids, gonadorelin agonists, microtubule active agents, nitrosoureas, lipid or protein kinase targeting agenst, IMiDs, protein or lipid phosphatase targeting agents, anti-angiogenic agents, Akt inhibitors, IGF-I inhibitors, FGF3 modulators, mTOR inhibitors, Smac mimetics, HDAC inhibitors, agents that induce cell differentiation, bradykinin 1 receptor antagonists, angiotensin II antagonists, cyclooxygenase inhibitors, heparanase inhibitors, lymphokine inhibitors, cytokine inhibitors, IKK inhibitors, P38MAPK inhibitors, HSP90 inhibitors, multlikinase inhibitors, bisphosphanate, rapamycin derivatives, anti-apoptotic pathway inhibitors, apoptotic pathway agonists, PPAR agonists, RAR agonists, inhibitors of Ras isoforms, telomerase inhibitors, protease inhibitors, metalloproteinase inhibitors, aminopeptidase inhibitors, SHIP activators—AQX-MN100, Humax-CD20 (ofatumumab), CD20 antagonists, IL2-diptheria toxin fusions, or combinations thereof.

In some embodiments, the second therapeutic agent is selected from ARRY-797, dacarbazine (DTIC), actinomycins $C_2$, $C_3$, D, and $F_1$, cyclophosphamide, melphalan, estramustine, maytansinol, rifamycin, streptovaricin, doxorubicin, daunorubicin, epirubicin, idarubicin, detorubicin, carminomycin, idarubicin, epirubicin, esorubicin, mitoxantrone, bleomycins A, $A_2$, and B, camptothecin, Irinotecan, Topotecan, 9-aminocamptothecin, 10,11-methylenedioxycamptothecin, 9-nitrocamptothecin, bortezomib, temozolomide, TAS 103, NPI0052, combretastatin, combretastatin A-2, combretastatin A-4, calicheamicins, neocarcinostatins, epothilones A B, C, and semi-synthetic variants, Herceptin, Rituxan, CD40 antibodies, asparaginase, interleukins, interferons, leuprolide, and pegaspargase, 5-fluorouracil, fluorodeoxyuridine, ptorafur, 5'-deoxyfluorouridine, UFT, MITC, S-1 capecitabine, diethylstilbestrol, tamoxifen, toremefine, tolmudex, thymitaq, flutamide, fluoxymesterone, bicalutamide, finasteride, estradiol, trioxifene, dexamethasone, leuproelin acetate, estramustine, droloxifene, medroxyprogesterone, megesterol acetate, aminoglutethimide, testolactone, testosterone, diethylstilbestrol, hydroxyprogesterone, mitomycins A, B and C, porfiromycin, cisplatin, carboplatin, oxaliplatin, tetraplatin, platinum-DACH, ormaplatin, thalidomide, lenalidomide, CI-973, telomestatin, CHIR258, Rad 001, SAHA, Tubacin, 17-AAG, sorafenib, JM-216, podophyllotoxin, epipodophyllotoxin, etoposide, teniposide, Tarceva, Iressa, Imatinib, Miltefosine, Perifosine, aminopterin, methotrexate, methopterin, dichloro-methotrexate, 6-mercaptopurine, thioguanine, azattuoprine, allopurinol, cladribine, fludarabine, pentostatin, 2-chloroadenosine, deoxycytidine, cytosine arabinoside, cytarabine, azacitidine, 5-azacytosine, gencitabine, 5-azacytosine-arabinoside, vincristine, vinblastine, vinorelbine, leurosine, leurosidine and vindesine, paclitaxel, taxotere and/or docetaxel.

In some embodiments, the second active agent is niacin, a fibrate, a statin, a Apo-A1 mimetic polypeptide (e.g., DF-4, Novartis), an apoA-I transcriptional up-regulator, an ACAT inhibitor, a CETP modulator, Glycoprotein (GP) IIb/IIIa receptor antagonists, P2Y12 receptor antagonists, Lp-PLA2-inhibitors, an anti-TNF agent, an IL-1 receptor antagonist, an IL-2 receptor antagonist, a cytotoxic agent, an immunomodulatory agent, an antibiotic, a T-cell co-stimulatory blocker, a disorder-modifying anti-rheumatic agent, a B cell depleting agent, an immunosuppressive agent, an anti-lymphocyte antibody, an alkylating agent, an anti-metabolite, a plant alkaloid, a terpenoids, a topoisomerase inhibitor, an antitumour antibiotic, a monoclonal antibody, a hormonal therapy (e.g., aromatase inhibitors), or combinations thereof.

In some embodiments, the second active is niacin, bezafibrate; ciprofibrate; clofibrate; gemfibrozil; fenofibrate; DF4 (Ac-D-W-F-K-A-F-Y-D-K-V-A-E-K-F-K-E-A-F-NH2); DF5; RVX-208 (Resverlogix); avasimibe; pactimibe sulfate (CS-505); CI-1011 (2,6-diisopropylphenyl[(2,4,6-triisopropylphenyl)acetyl]sulfamate); CI-976 (2,2-dimethyl-N-(2,4,6-trimethoxyphenyl)dodecanamide); VULM1457 (1-(2,6-diisopropyl-phenyl)-3-[4-(4'-nitrophenylthio)phenyl]urea); CI-976 (2,2-dimethyl-N-(2,4,6-trimethoxyphenyl)dodecanamide); E-5324 (n-butyl-N'-(2-(3-(5-ethyl-4-phenyl-1H-imidazol-1-yl)propoxy)-6-methylphenyl)urea); HL-004 (N-(2,6-diisopropylphenyl)tetradecylthioacetamide); KY-455 (N-(4,6-dimethyl-1-pentylindolin-7-yl)-2,2-dimethylpropanamide); FY-087 (N-[2-[N'-pentyl-(6,6-dimethyl-2,4-heptadiynyl)amino]ethyl]-(2-methyl-1-naphthyl-thio)acetamide); MCC-147 (Mitsubishi Pharma); F 12511 ((S)-2',3',5'-trimethyl-4'-hydroxy-alpha-dodecylthioacetanilide); SMP-500 (Sumitomo Pharmaceuticals); CL 277082 (2,4-difluoro-phenyl-N[[4-(2,2-dimethylpropyl)phenyl]methyl]-Nepthyl)urea); F-1394 ((1s,2s)-2-[3-(2,2-dimethylpropyl)-3-nonylureido]aminocyclohexane-1-yl 3-[N-(2,2,5,5-tetramethyl-1,3-dioxane-4-carbonyl)amino]propionate); CP-113818 (N-(2,4-bis(methylthio)-6-methylpyridin-3-yl)-2-(hexylthio)decanoic acid amide); YM-750; torcetrapib; anacetrapid; JTT-705 (Japan Tobacco/Roche); abciximab; eptifibatide; tirofiban; roxifiban; variabilin; XV 459 (N(3)-(2-(3-(4-formamidinophenyl)isoxazolin-5-yl)acetyl)-N(2)-(1-butyloxycarbonyl)-2,3-diaminopropionate); SR 121566A (3-[N-{4-[4-(aminoiminomethyl)phenyl]-1,3-thiazol-2-yl}-N-(1-carboxymethylpiperid-4-yl)aminol propionic acid, trihydro chloride); FK419 ((S)-2-acetylamino-3-[(R)-[1-[3-(piperidin-4-yl)propionyl]piperidin-3-ylcarbonyl]amino] propionic acid trihydrate); clopidogrel; prasugrel; cangrelor; AZD6140 (AstraZeneca); MRS 2395 (2,2-Dimethyl-propionic acid 3-(2-chloro-6-methylaminopurin-9-yl)-2-(2,2-dimethyl-propionyloxymethyl)-propyl ester); BX 667 (Berlex Biosciences); BX 048 (Berlex Biosciences); darapladib (SB 480848); SB-435495 (GlaxoSmithKline); SB-222657 (GlaxoSmithKline); SB-253514 (GlaxoSmithKline); alefacept, efalizumab, methotrexate, acitretin, isotretinoin, hydroxyurea, mycophenolate mofetil, sulfasalazine, 6-Thioguanine, Dovonex, Taclonex, betamethasone, tazarotene, hydroxychloroquine, sulfasalazine, etanercept, adalimumab, infliximab, abatacept, rituximab, trastuzumab, Anti-CD45 monoclonal antibody AHN-12 (NCI), Iodine-131 Anti-B1 Antibody (Corixa Corp.), anti-CD66 monoclonal antibody BW 250/183 (NCI, Southampton General Hospital), anti-CD45 monoclonal antibody (NCI, Baylor College of Medicine), antibody anti-anb3 integrin (NCI), BIW-8962 (BioWa Inc.), Antibody BC8 (NCI), antibody muJ591 (NCI), indium In 111 monoclonal antibody MN-14 (NCI), yttrium Y 90 monoclonal antibody MN-14 (NCI), F105 Monoclonal Antibody (NIAID), Monoclonal Antibody RAV12 (Raven Biotechnologies), CAT-192 (Human Anti-TGF-Beta1 Monoclonal Antibody, Genzyme), antibody 3F8 (NCI), 177Lu-J591 (Weill Medical College of Cornell University), TB-403 (BioInvent International AB), anakinra, azathioprine, cyclophosphamide, cyclosporine A, leflunomide, d-penicillamine, amitriptyline, or nortriptyline, chlorambucil, nitrogen mustard, prasterone, LJP 394 (abetimus sodium), LJP 1082 (La Jolla Pharmaceutical), eculizumab, belibumab, rhuCD40L (NIAID), epratuzumab, sirolimus, tacrolimus, pimecrolimus, thalidomide, antithymocyte globulin-equine (Atgam, Pharmacia Upjohn), antithymocyte globulin-rabbit (Thymoglobulin, Genzyme), Muromonab-CD3 (FDA Office of Orphan Products Development), basiliximab, daclizumab, riluzole, cladribine, natalizumab, interferon beta-1b, interferon beta-1a, tizanidine, baclofen, mesalazine, asacol, pentasa, mesalamine, balsalazide, olsalazine, 6-mercaptopurine, AIN457 (Anti IL-17 Monoclonal Antibody, Novartis), theophylline, D2E7 (a human anti-TNF mAb from Knoll Pharmaceuticals), Mepolizumab (Anti-IL-5 antibody, SB 240563), Canakinumab (Anti-IL-1 Beta Antibody, NIAMS), Anti-IL-2 Receptor Antibody (Daclizumab, NHLBI), CNTO 328 (Anti IL-6 Monoclonal Antibody, Centocor), ACZ885 (fully human anti-interleukin-1 beta monoclonal antibody, Novartis), CNTO 1275 (Fully Human Anti-IL-12 Monoclonal Antibody, Centocor), (3S)-N-hydroxy-4-({4-[(4-hydroxy-2-butynyl)oxy]phenyl}sulfonyl)-2,2-dimet-hyl-3-thiomorpholine carboxamide (apratastat), golimumab (CNTO 148), Onercept, BG9924 (Biogen Idec), Certolizumab Pegol (CDP870, UCB Pharma), AZD9056 (AstraZeneca), AZD5069 (AstraZeneca), AZD9668 (AstraZeneca), AZD7928 (AstraZeneca), AZD2914 (AstraZeneca), AZD6067 (AstraZeneca), AZD3342 (AstraZeneca), AZD8309 (AstraZeneca),), [(1R)-3-methyl-1-({(2S)-3-phenyl-2-[(pyrazin-2-ylcarbonyl)amino]propanoyl}amino)butyl]boronic acid (Bortezomib), AMG-714, (Anti-IL 15 Human Monoclonal Antibody, Amgen), ABT-874 (Anti IL-12 monoclonal antibody, Abbott Labs), MRA(Tocilizumab, an Anti IL-6 Receptor Monoclonal Antibody, Chugai Pharmaceutical), CAT-354 (a human anti-interleukin-13 monoclonal antibody, Cambridge Antibody Technology, MedImmune), aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, flurobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, celecoxib, rofecoxib, valdecoxib, parecoxib, etoricoxib, lumiracoxib, CS-502 (Sankyo), JTE-522 (Japan Tobacco Inc.), L-745,337 (Almirall), NS398 (Sigma), betamethasone (Celestone), prednisone (Deltasone), alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, formoterol, halcinonide, halometasone, hydrocortisone, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone, rimexolone, tixocortol, triamcinolone, ulobetasol; cisplatin; carboplatin; oxaliplatin; mechlorethamine; cyclophosphamide; chlorambucil; vincristine; vinblastine; vinorelbine; vindesine; azathioprine; mercaptopurine; fludarabine; pentostatin; cladribine; 5-fluorouracil (5FU); floxuridine (FUDR); cytosine arabinoside; methotrexate; trimethoprim; pyrimethamine; pemetrexed; paclitaxel; docetaxel; etoposide; teniposide; irinotecan; topotecan; amsacrine; etoposide; etoposide phosphate; teniposide; dactinomycin; doxorubicin; daunorubicin; valrubicine; idarubicine; epirubicin; bleomycin; plicamycin; mitomycin; trastuzumab; cetuximab; rituximab; bevacizumab; finasteride; goserelin; aminoglutethimide; anastrozole; letrozole; vorozole; exemestane; 4-androstene-3,6,17-trione ("6-OXO"; 1,4,6-androstatrien-3,17-dione (ATD); formestane; testolactone; fadrozole; or combinations thereof.

In some embodiments, the second therapeutic agent is an antibiotic. In some embodiments, the second therapeutic agent is an anti-bacterial agent. In some embodiments, the second therapeutic agent is amikacin, gentamicin, kanamycin, neomycin, netilmicin, streptomycin, tobramycin, paromomycin, geldanmycin, herbimycin, loracarbef, ertapenem, doripenem, imipenem, cilastatin, meropenem, cefadroxil, cefazolin, cefalotin, cefalexin, cefaclor, cefamandole, cefoxitin, defprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, teicoplanin, vancomycin, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, meticillin, nafcillin, oxacillin, penicillin, piperacillin, ticarcillan, bacitracin, colistin, polymyxin B, ciprofloxacin, enoxacin, gatifloxacin, levofloxacin, lomefloxacin, moxifloxacin, norfloxacin, ofloxacin, trovfloxacin, mafenide, prontosil, sulfacetamide, sulfamethizole, sulfanimilimde, sulfsalazine, sulfsioxazole, trimethoprim, demeclocycline, doxycycline, minocycline, oxtetracycline, tetracycline, arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinuspristin/dalfopristin, rifampin, tinidazole, and combinations thereof.

In some embodiments, the second therapeutic agent is an antibiotic. In some embodiments, the second therapeutic agent is an anti-viral agent. In some embodiments, the second therapeutic agent is acyclovir, famciclovir, valacyclovir, abacavir, aciclovir, adfovir, amantadine, amprenavir, arbidol., atazanavir, artipla, brivudine, cidofovir, combivir, edoxudine, efavirenz, emtricitabine, enfuvirtide, entecavir, fomvirsen, fosamprenavir, foscarnet, fosfonet, ganciclovir, gardasil, ibacitabine, imunovir, idoxuridine, imiquimod, indinavir, inosine, integrase inhibitors, interferons, including interferon type III, interferon type II, interferon type I, lamivudine, lopinavir, loviride, MK-0518, maraviroc, moroxydine, nelfinavir, nevirapine, nexavir, nucleoside analogues, oseltamivir, penciclovir, peramivir, pleconaril, podophyllotoxin, protease inhibitors, reverse transcriptase inhibitors, ribavirin, rimantadine, ritonavir, saquinavir, stavudine, tenofovir, tenofovir disoproxil, tipranavir, trifluridine, trizivir, tromantadine, truvada, valganciclovir, vicriviroc, vidarabine, viramidine, zalcitabine, zanamivir, zidovudine, and combinations thereof.

In some embodiments, the second therapeutic agent is an antibiotic. In some embodiments, the second therapeutic agent is an anti-fungal agent. In some embodiments, the second therapeutic agent is amrolfine, utenafine, naftifine, terbinafine, flucytosine, fluconazole, itraconazole, ketoconazole, posaconazole, ravuconazole, voriconazole, clotrimazole, econazole, miconazole, oxiconazole, sulconazole, terconazole, tioconazole, nikkomycin Z, caspofungin, micafungin, anidulafungin, amphotericin B, liposomal nystastin, pimaricin, griseofulvin, ciclopirox olamine, haloprogin, tolnaftate, undecylenate, clioquinol, and combinations thereof.

In some embodiments, the second therapeutic agent is an antibiotic. In some embodiments, the second therapeutic agent is an anti-parasitic agent. In some embodiments, the second therapeutic agent is amitraz, amoscanate, avermectin, carbadox, diethylcarbamizine, dimetridazole, diminazene, ivermectin, macrofilaricide, malathion, mitaban, oxamniquine, permethrin, praziquantel, prantel pamoate, selamectin, sodium stibogluconate, thiabendazole, and combinations thereof.

In some embodiments, an HC•HA complex disclosed herein (e.g., nHC•HA and/or rcHC•HA) is co-administered with a tissue transplant. In some embodiments, an HC•HA complex disclosed herein (e.g., nHC•HA and/or rcHC•HA) is co-administered with a stem cell transplant. In some embodiments, an HC•HA complex disclosed herein (e.g., nHC•HA and/or rcHC•HA) is co-administered with an organ transplant.

In some embodiments, an HC•HA complex disclosed herein (e.g., nHC•HA and/or rcHC•HA) is administered concurrently (e.g., simultaneously, essentially simultaneously or within the same treatment protocol) with a tissue transplant. In some embodiments, an HC•HA complex disclosed herein (e.g., nHC•HA and/or rcHC•HA) is administered before or after a tissue transplant. In some embodiments, the time period between administration of an HC•HA complex disclosed herein (e.g., nHC•HA and/or rcHC•HA) and the tissue transplant ranges from a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval. In some embodiments, the timing between the administration of an HC•HA complex disclosed herein (e.g., nHC•HA and/or rcHC•HA) and a second active agent is about less than an hour, less than a day, less than a week, or less than a month.

In some embodiments, an HC•HA complex disclosed herein (e.g., nHC•HA and/or rcHC•HA) is co-administered with a tissue transplant and an immuno-suppressive agent. In some embodiments, an HC•HA complex disclosed herein (e.g., nHC•HA and/or rcHC•HA) is co-administered with a tissue transplant and a calcineurin inhibitor (e.g., cyclosporin or tacrolimus); an mTOR inhibitor (sirolimus; everolimus); an anti-proliferative agent (azathioprine or mycophenolic acid); a corticosteroid (e.g., prednisolone or hydrocortisone); a monoclonal anti-IL-2Rα receptor antibody (e.g., basiliximab or daclizumab); a polyclonal anti-T-cell antibodies (e.g., anti-thymocyte globulin (ATG) or anti-lymphocyte globulin (ALG)); or combinations thereof.

In some embodiments, a tissue is coated with an HC•HA complex disclosed herein (e.g., nHC•HA and/or rcHC•HA). In some embodiments, a plurality of stem cells are coated with an HC•HA complex disclosed herein (e.g., nHC•HA and/or rcHC•HA). In some embodiments, an organ is coated with an HC•HA complex disclosed herein (e.g., nHC•HA and/or rcHC•HA). In some embodiments, coating a tissue with an HC•HA complex disclosed herein prevent a tissue from being acted upon by the host immune system.

In some embodiments, an organ, tissue, or plurality of stem cells is contacted with an HC•HA complex disclosed herein. In some embodiments, an organ, tissue, or plurality of stem cells is contacted with a composition comprising an HC•HA complex disclosed herein (e.g., nHC•HA and/or rcHC•HA). In some embodiments, the composition has a pH of about 7.0 to about 7.5. In some embodiments, the composition has a pH of 7.4. In some embodiments, the composition further comprises potassium, magnesium, and Raffinose. In some embodiments, the composition further comprises at least one of adenosine, glutathine, allopurinol, and hydroxyethyl starch. In some embodiments, the composition is UW solution supplemented with an HC•HA complex disclosed herein.

In some embodiments, the organ, tissue, or plurality of stem cells are contacted with an HC•HA complex disclosed herein (e.g., nHC•HA and/or rcHC•HA) for about 30 minutes, about 1 hour, about 2 hours, about 3 hours, about 4 hours, about 5 hours, about 6 hours, about 12 hours, about 24 hours, about 36 hours, or about 48 hours. In some embodiments, the contacting occurs at a temperature that protects tissues and vascular conditioning (e.g., less than ambient temperature). In some embodiments, the contacting occurs at 4° C.

EXAMPLES

Preparation of AME, and AMP

All procedures for the above materials are carried out aseptically.

Frozen human AM obtained from Bio-tissue (Miami, Fla.) is washed 2-3 times with PBS to remove the storage medium. To prepare AME, AM is weighed (~10 mg/cm2), transferred to a sterile 50 ml centrifuge tube and centrifuged at 4° C. for 5 min at 5000×g to remove the excess fluid. AM is weighed, transferred to a 100 mm or 150 mm sterile Petri dish, and frozen in the air phase of a liquid nitrogen container for 20 min before being sliced into small pieces with a disposable scalpel and homogenized with Tissue Tearor (Biospec Products, Inc., Dremel, Wis.) in PBS. The homogenate is mixed at 4° C. for 30 min and centrifuged at 15,000×g for 30 min. The supernatant is collected, designated as AME, and stored in aliquots (0.5 ml) at −80° C.

To prepare lyophilized AMP, AME is lyophilized by SpeedVac (Savant Instruments Inc., Farmingdale, N.Y.) at 4° C. for 4 h to remove 89% of weight due to water and stored at −80° C.

Example 1

Sequential AM Extraction

Cryopreserved human AM, obtained from Bio-tissue, Inc. (Miami, Fla.), was sliced into small pieces, frozen in liquid nitrogen, and ground to fine powder by a BioPulverizer. The powder was mixed with Buffer A (100 mM Tris-HCl, pH 7.6, 150 mM NaCl, 4 mM EDTA, 1% (v/v) Triton X-100) at 1:1 (g/ml) at 4° C. for 1 h. The mixture was centrifuged at 48,000×g for 30 min at 4° C. and the supernatant (Extract A) stored at −80° C. The pellet was then washed three times with Buffer A before being extracted with Buffer B (100 mM Tris-HCl, pH 7.6, 1 M NaCl, 4 mM EDTA, 1% (v/v) Triton X-100) at 4° C. for 1 h. After the centrifugation, the supernatant (Extract B) was stored. The remaining pellet was washed with Buffer B before adding Buffer C (100 mM sodium acetate, pH 5.8, 4 M guanidine hydrochloride, 4 mM EDTA, 1% Triton X-100) at 4° C. for 24 h. Again after the centrifugation, the supernatant (Extract C) was stored. Buffers A, B, and C were supplemented with the following protease and phosphatase inhibitors: protease inhibitor cocktail (1:100 dilution according to manufacturer's suggestion), 0.5 mM PMSF, 50 mM sodium fluoride, and 0.2 mM sodium vanadate. Protein concentrations in AM extracts were determined by BCA Protein Assay Kit, while HA concentrations by an ELISA-based HA Quantitative Test Kit.

Example 2

Purification of Native (nHC•HA) Complex

The whole procedure for preparation of human AM extracts was carried out aseptically for subsequent cell culture-based experiments as recently reported. Most of preparation steps were the same as described above with the following modifications. The AM powder was mixed with the cold PBS buffer without protease inhibitors at 1:1 (g/ml). The mixture was centrifuged at 48,000×g 4° C. for 30 min. The supernatant was designated as Extract P.

Extract P (prepared in PBS) was dissolved in CsCl/4M guanidine HCl mixture at the initial density of 1.35 g/ml, and centrifuged at 125,000×g for 48 h at 15° C. A total of 15 fractions (0.8 ml/fraction) were collected from the top to the bottom of each tube. Besides the density, the concentration of proteins and HA in each fraction was measured by BCA Protein Assay and HA Quantitative Test Kit, respectively. Fractions #8-15, which contain HA but no detectable proteins, were pooled, adjusted with CsCl/4M guanidine HCl at the initial density of 1.40 g/ml, centrifuged, and fractionated in the same manner as described above. Fractions #3-15, which contained HA but no detectable proteins, were pooled and dialyzed against distilled water to remove CsCl and guanidine HCl. The dialysate was mixed with 3 volumes of 95% (v/v) ethanol containing 1.3% (w/v) potassium acetate at 0° C. for 1 h. After centrifugation at 15,000×g, the pellet was washed with 70% (v/v) ethanol and centrifugation. The pellet was briefly dried by air, stored at −80° C., and designated as the nHC•HA complex.

Example 3

Biochemical Characterization of HC•HA Covalent Complex and its Association with TSG-6 in AME Amniotic membrane was obtained from three separate donors. The amniotic membrane was extracted sequentially with Buffers A, B, and C, which consisted of increasing salt concentrations (0.15 M NaCl, 1.0 M NaCl, and 4 M Guanidine HCl, respectively). ELISA-based HA Quantitative Test and BCA Protein Assay were then used to measure HA and protein levels of these 3 extracts.

The result showed that HA was present in all, but was mostly (more than 70%) extracted by Buffer A in the water-soluble Extract A as well as in AME, resulting a much higher ratio of HA/protein, and had an average MW of 6×10$^6$ Daltons (Da).

Because inter-α-inhibitor (IαI) is a natural inhibitor of HAase, we confirmed the presence of IαI in AM stroma by immunostaining.

Western blotting showed purified IαI (FIG. 1B, lane 2) consisted of a major band at ~250 kDa, representing the intact IαI, and several bands with smaller MWs, which are presumably degradation products of IαI. Without treatment (None), Extract A contained a band corresponding to IαI, but also had a HMW band, which as shown below was a complex formed by HMW HA and HC of IαI (HC•HA complex), which could not enter the gel due to its large size, and two other major bands of 75 kDa (corresponding to a free HC) and 120 kDa (consisting of one HC covalently coupled to either the bikunin or TSG-6) (FIG. 1B, lane 3). Similar findings were noted in Extract C (FIG. 1B, lane 5) but not in Extract B (FIG. 1B, lane 4). To further characterize an HC•HA complex, we used HAase to digest HA into small fragments so that HC could enter the gel. HAase digestion (FIG. 1B, lanes 6-8) completely removed an HC•HA complex retained in the well to yield a 75 kDa HC band in Extracts A, B and C. We also used 0.02 N NaOH for 1 h to hydrolyze any ester bond formed between HCs and HA, and noted that such a treatment caused a large reduction of IαI-immunoreactive bands, with the exception of the 120 kDa species, and dramatically increased the intensity of 75 kDa HC band. (FIG. 1B, lanes 9-11).

A similar result was found in AME prepared by low speed (15,000×g, L) or high speed (48,000×g, H) centrifugation (FIG. 1D).

Example 4

Biochemical Purification of HC•HA Complex from AME

We used Microcon centrifugal spin columns with 30, 50, or 100 kDa MW cutoff (Millipore, Billerica, Mass.) to obtain "filtrate" and "retentate" from AME. We noted that TGF-β1 promoter activity was significantly suppressed by the retentate, but not by the filtrate, of these three MW cutoffs up to 100 kDa. This result suggested that the suppressive activity was retained in HMW complex greater than 100 kDa.

To test this hypothesis, we purified an HC•HA complex by submitting AME to two successive rounds of CsCl ultracentrifugation in the presence of 4M Guanidine HCl with the initial density of 1.35 g/ml and 1.40 g/ml, respectively.

After ultracentrifugation, each tube was subdivided into a total of 15 fractions (from the low density to high density) and monitored by ELISA-based HA Quantitative Test and BCA Protein Assay for HA and protein contents, respectively. We pooled those fractions that contained HA but no proteins from these two runs. As a result, Fractions #8-15 were pooled from the first round before subjecting to the second round. Similarly, Fractions #4-15 were pooled from the second round and designated it as "Purified HC•HA Complex".

Compared to AME, which started with 1370 μg of protein and 62 μg of HA per ml, Purified HC•HA complex did not contain detectable proteins. Even if it was 10 fold concentrated, purified HC•HA complex still did not contain proteins detectable by the BCA Protein Assay. Judged by the detection limit of the BCA assay of being 25 μg/ml, we estimated that our biochemical purification resulted in at least 550 folds purification.

Figure 4:
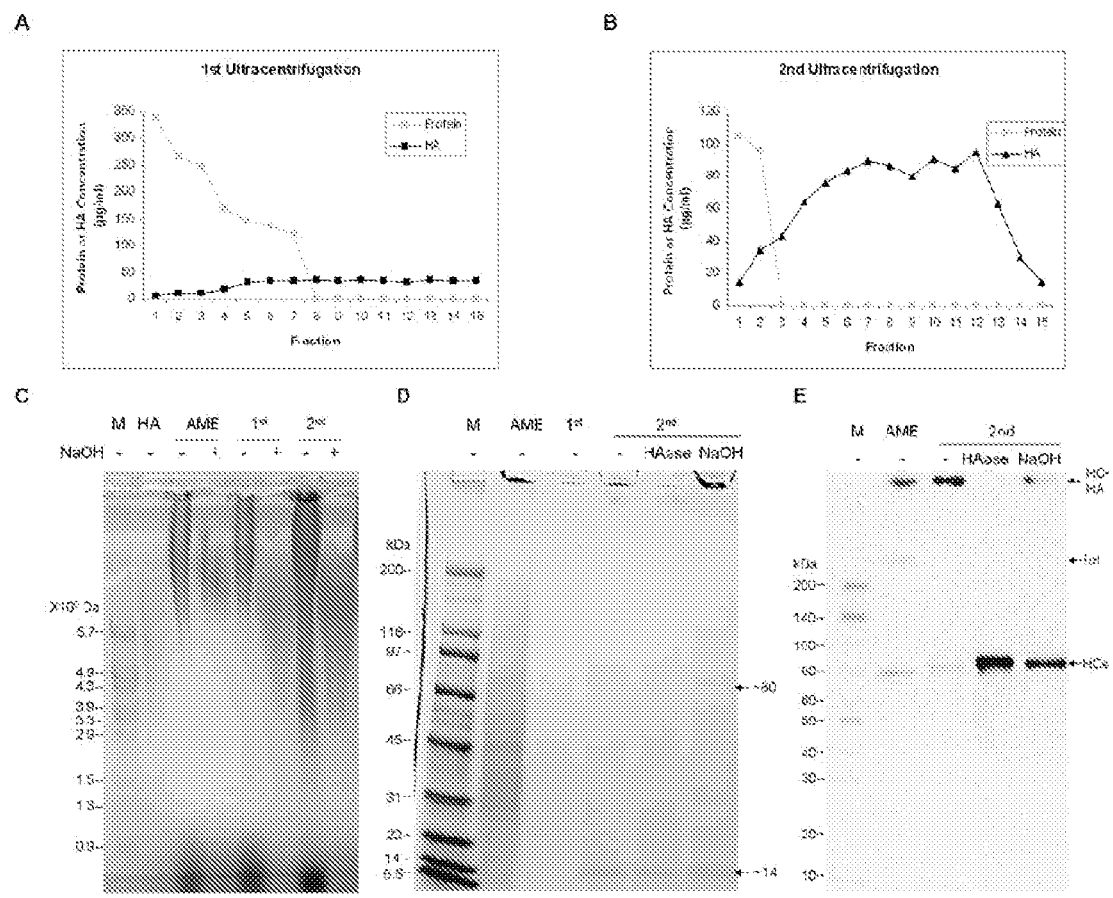
FIG. 4. Fraction#8-15 from the first CsCl/4M guanidine HCl ultracentrifugation (1st) started at the initial density of 1.35 g/ml (A) and Fraction#3-15 from the second ultracentrifugation (2nd) started at the initial density of 1.40 g/ml (B) were pooled according to the presence of HA but the absence of proteins. The latter fraction, after dialysis and removal of water, was designated as the nHC•HA complex, treated with or without 0.05 N NaOH at 25° C. for 1 h, and analyzed on 0.5% agarose gel before being stained with All-stains dye (C), stained with the Coomassie blue dye (D), or on the western blot using an anti-IαI antibody (E). The results confirmed the nHC•HA complex was formed by HMW HA and HC of IαI via a NaOH-sensitive bond. Please note the pooled fractions from the second ultracentrifugation (labeled as 2nd) in D were concentrated ~20 fold by lyophilized before loading to enhance the detection by the Coomassie blue dye.

Agarose gel analysis confirmed that HA in purified HC•HA complex was of HMW species, had an average MW of greater than $1\times10^6$ Da (FIG. 4C). Purified HC•HA was concentrated by ~20 fold before loading on SDS-PAGE. Subsequent Coomassie blue staining confirmed that except for the visible band corresponding to individual HC (75~80 kDa), there were few visible protein bands in purified HC•HA complex (FIG. 4D). The identity of this protein band being HC was further confirmed by Western blot analysis (FIG. 4E). Purified HC•HA complex was detected in the well (unable to enter the gel due to its HMW in association with HA) (c.f. FIGS. 4D and 4E), but disappeared completely after HAase digestion and partially by NaOH treatment. Meanwhile the intensity of the HC band (75~80 kDa) was markedly enhanced because it was released from HMW HA or because the ester bond formed between HC and HA was broken, respectively (FIG. 4E).

Western blot analysis with an anti-TSG-6 antibody did not detect any TSG-6 in the preparation of purified HC•HA complex.

Example 5

In Vitro Reconstitution of HC•HA Complex (rcHC•HA)

To further define the biological function of purified HC•HA complex, we reconstituted the HA•HC complex in vitro using three defined components including HMW HA (Healon™, Advanced Medical Optics, CA), IAI (purified by our laboratory), and TSG-6 (kindly provided by Dr. Anthony J Day).

HABP (HA binding protein) is crosslinked to Covalink-NH 96 well. In brief, Covalink-NH plates (NUNC, Placerville, N.J.) are sterilized and dried in 70% alcohol for 2 h before being added with 50 μl of 0.184 mg/ml Sulfo-NHS (Pierce, Rockford, Ill.) in distilled $H_2O$ containing 0.04 mg/ml HABP (Seikagaku corporation, Tokyo, Japan) per 96-well. The crosslinking was performed by adding 1 μl of 0.123 mg/ml 1-ethy-1-3(3-dimethylaminopropyl)carbidodi-imide (EDAC) in distilled H2O per well. The plate is incubated overnight at 4° C. or for 2 h at 23° C. before the coupling solution is removed, and washed 3× with PBS containing 2 M NaCl and 50 mM MgSO4 followed by 3× washes with PBS.

To determine the maximal HA binding capacity, HABP cross-linked plates are used immediately by adding 50 μl of 1.5 to 200 μg/ml of HMW HA (>4×106 Da, Advanced Medical Optics, Santa Ana, Calif.) in PBS with 5 mM MgCl2 with or without 40 μg/ml human IαI (purified by our laboratory) and/or 6 μg/ml recombinant human TSG-6 (provided by Dr. A. J. Day). The mixture is incubated at 25° C. for 24 h, and the unbound component is removed by 4× PBS washes. The bound HA was quantitated by the same HA kit and subjected to HAase digestion or NaOH treatment before Western blotting.

Figure 5:
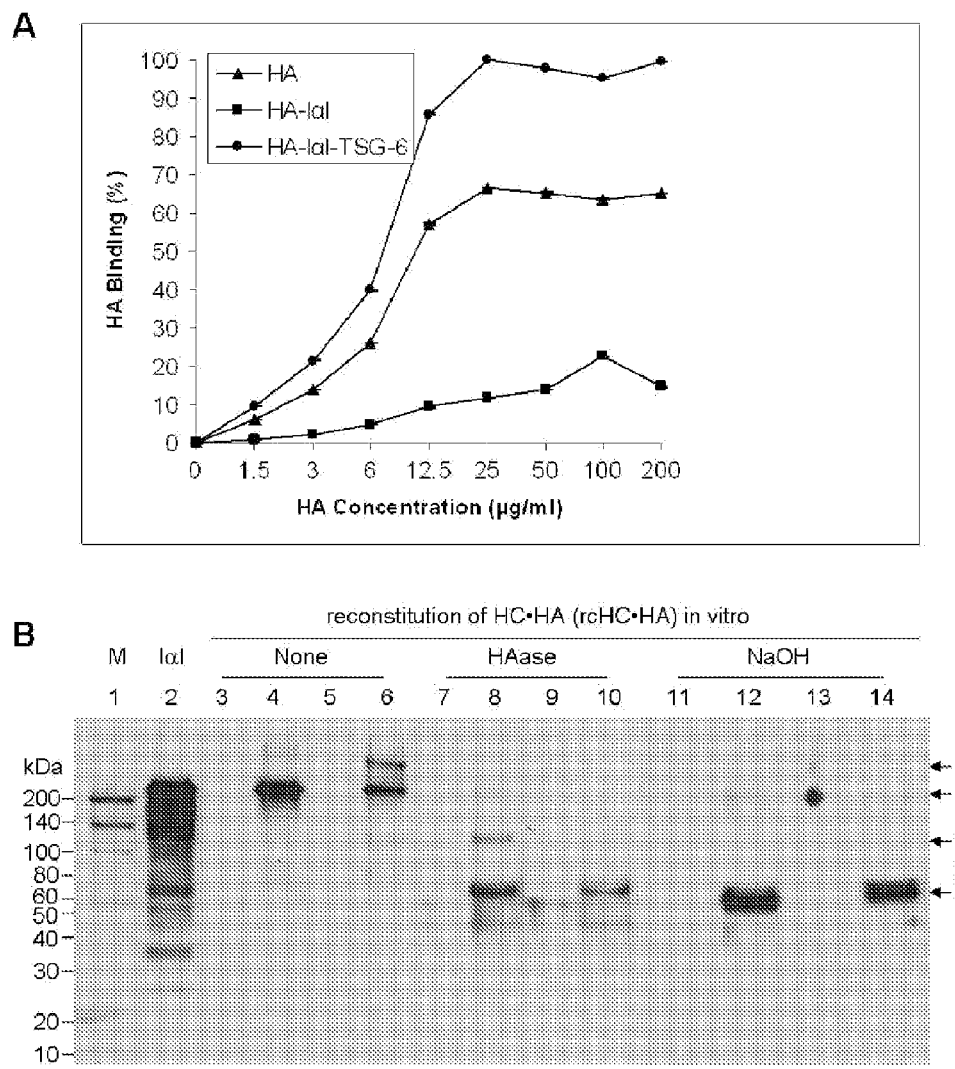
FIG. 5. The HA binding capacity (%) on HABP-crosslinked wells was determined to be maximal at 25 μg/ml of HMW HA by addition of both human IαI and recombinant human TSG-6 (A, ●) when compared to HMW HA alone (A, ▲) or HMW HA with IαI (A, ■). Western blot using an anti-IαI antibody (B) revealed that the bound HMW HA on HABP-crosslinked wells formed HC•HA complex when added with both IαI and TSG-6 (HA+IαI+TSG-6, lanes 6, 10, and 14) when compared to HMW HA alone (lanes 3, 7, and 11), with IαI alone (HA+IαI, lanes 4, 8, 12) or TSG-6 alone (HA+TSG-6, lanes 5, 9, 13) either without (lanes 3-6) or with HAase digestion (lanes 7-10) or NaOH treatment (lanes 11-14).

We then added 50 μl of serial concentrations of 1.5 to 200 μg/ml of HMW HA alone (▲) or with additional 40 μg/ml concentration of IαI alone (■) or both 40 μg/ml IαI and 6 μg/ml TSG-6 (●) (FIG. 5A).

After washing, the ELISA-based HA Quantitative Test showed that the quantity of bound HA was significantly decreased when added with IαI, but significantly increased when added with both IαI and TSG-6. This result is consistent with the notion that addition of IαI alone might interfere with HA's binding with HABP, while addition of TSG-6 facilitates cross-linking between HA and IαI, hence promoting binding with HABP.

The above result also indicated that in vitro reconstitution of HA-containing complex onto immobilized plastic surface is optimized by reaching 100% binding capacity when 25 μg/ml of HMW HA was used (FIG. 5A).

Based on the above data, we applied the same volume of 50 μl of 25 μg/ml HMW HA to each well of the above conditions (FIG. 5A). After extensive washing to remove unbound components, each well containing the bound HA was subjected to 50 units/ml HAase digestion or 0.05 N NaOH treatment as mentioned above, and solubilized in the Laemmli sample buffer for Western blotting with an anti-IαI antibody. As compared to IαI (FIG. 5B, lane 2) and HMW HA alone (FIG. 5B, lane 3), intact IαI, but not its degraded fragments, was present in the HABP/HA-coated wells and retained after extensive washing (FIG. 5B, lane 4). As expected, there was no IαI-immunoreactive band where HA was added with TSG-6 alone (FIG. 5B, lane 5).

Importantly, when HA, IαI, and TSG-6 were incubated together (FIG. 5B, lane 6), an additional HMW band was seen at bottom of the loading well while the intensity of the IαI band was reduced, presumably because some IαI had been consumed in the transfer of HC to HMW HA by TSG-6. This HC•HA band and IαI were eliminated by HAase digestion (FIG. 5B, lane 10) or NaOH treatment (FIG. 5B, lane 14), resulting in the release (appearance) of a ~75-80-kDa HC band.

By a comparison, intact IαI (FIG. 5B, lane 4) was digested by HAase into at least two bands including a higher MW 120-kDa band and ~75-80-kDa band, where the former is likely to correspond to a HC•bikunin complex linked by chondroitin sulfate since it was cleavable by NaOH (FIG. 5B, lane 12) but resistance to hyaluronidase treatment (FIG. 5B, lane 8).

These data verified that an HC•HA complex could be effectively reconstituted in vitro from HA and IαI in the presence of TSG-6. Once the complex was formed, TSG-6 was not covalently associated in this complex as it can be washed away, a finding that was supported by Western blotting using an anti-TSG-6 antibody.

Example 6

Figure 7:
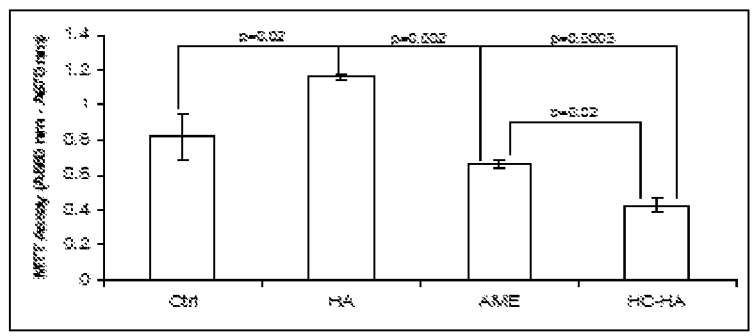
FIG. 7. The MTT assay showed that HC•HA complex purified from AME (labeled as HC-HA) significantly decreased the cell viability more so than HMW HA or AME alone (P=0.002 and 0.02, respectively).
Figure 8:
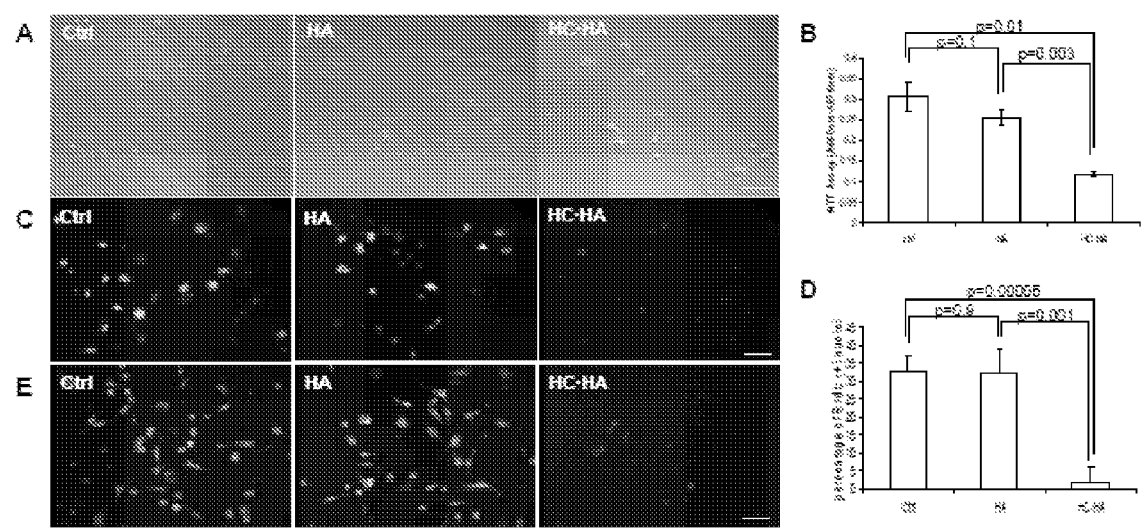
FIG. 8. The morphology of HUVEC cells is changed by an HC•HA complex but not by HMW HA. When an HC•HA complex was simultaneously with HUVEC seeding, HUVEC maintained a typical polyhedral shape without (Ctrl) or with 4 μg/ml HMW HA for 2 days (HA). In contrast, HUVEC became small, rounded and aggregated with 4 μg/ml HC•HA complex for 2 days.
Figure 9:
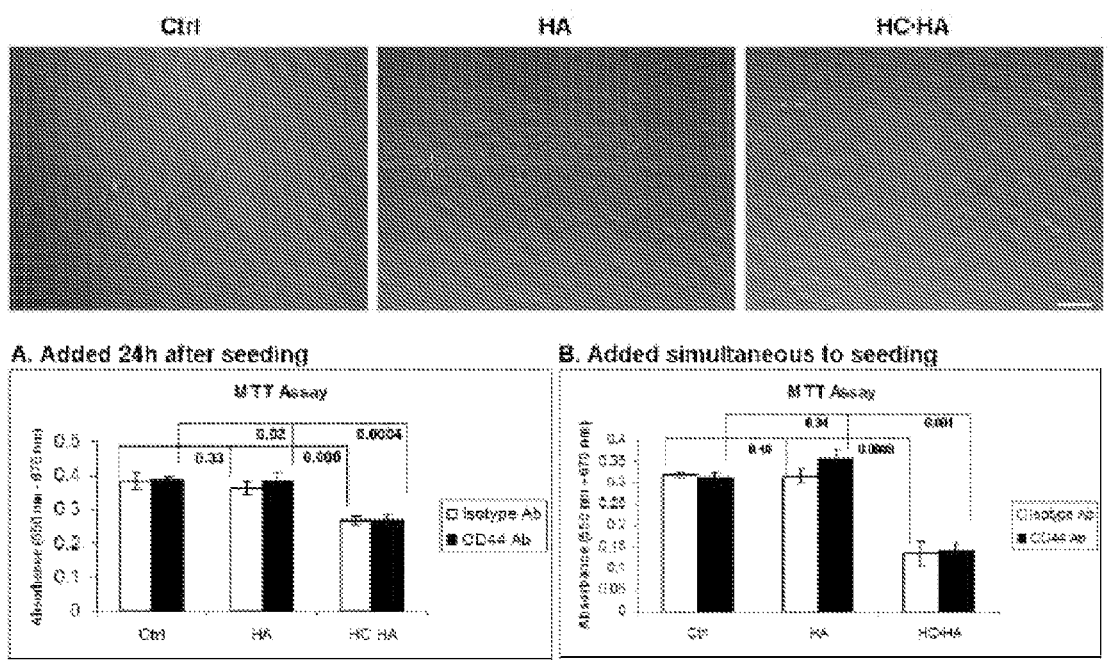
FIG. 9. When the HC•HA complex was added 24 h after HUVEC seeding, it did not cause the same morphological rounding when compared to the plastic control (Ctrl) or HMW HA as noted when the HC•HA complex was added simultaneously with HUVEC seeding (c.f., FIG. 9, phase contrast micrographs. However, addition of the HC•HA complex caused significant reduction of viability (based on the MTT assay) when compared to Ctrl and HMW HA (FIG. 9A). Interestingly, preincubation of the antibody blocking CD44 did not affect the reduction of HUVEC viability caused by the HC•HA complex (FIG. 9A). Pre-incubation of the antibody blocking CD44 did not alter the reduction of HUVEC viability (by the MTT) (FIG. 9B).
Figure 10:
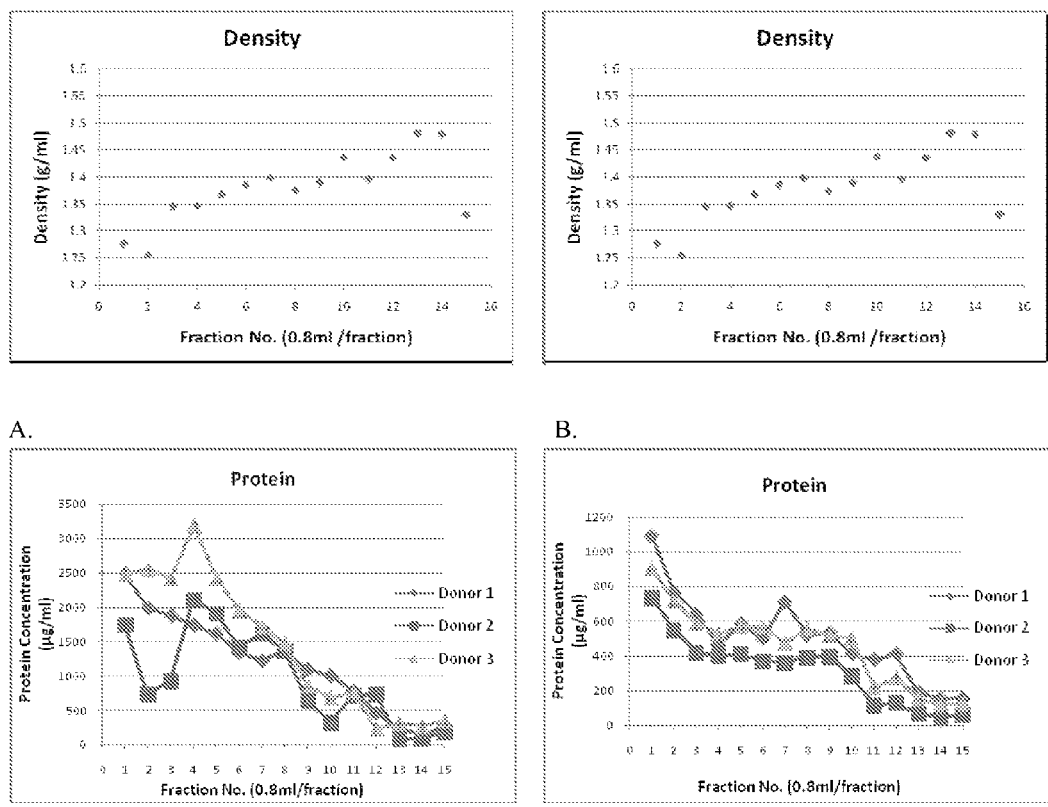
FIG. 10. Protein Density and Concentration after $1^{st}$ (A) and $2^{nd}$ (B) round of Ultracentrifugation. CH extract/CsCl/4M (1.35 g/ml) guanidine mixtures for 3 donors were centrifuged at 125000 g for 48 h at 15° C. Fractions were collected from the top to the bottom of each tube (15 fractions, 0.8 ml/fraction). The weight and proteins in each fraction were measured and fractions 9-15, which contained minimal proteins were pooled. The pooled sample was adjusted with CsCl and guanidine-HCl (1.40 g/ml) and centrifuged again as above. Fractions were collected and proteins were measured. Fractions 13-15, which contained minimal proteins, were pooled and dialyzed to distill water to remove CsCl and guanidine.
Figure 11:
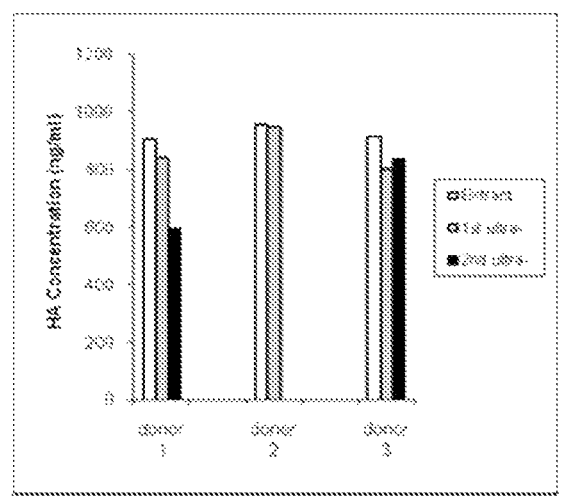
FIG. 11. HA Concentration in extract and after $1^{st}$ and $2^{nd}$ round of Ultracentrifugation. The HA concentration of extract before centrifugation and after the $1^{st}$ and $2^{nd}$ round of ultracentrifugation for 3 donors were measured by HA ELISA. The purified HA complex was stored at −80° C. and used for further biochemical characterization.

Anti-Inflammatory and Anti-Scarring Actions of HC•HA Complex Purified from AME or in Vitro Reconstitution For mouse macrophage RAW264.7 cells, HC•HA complex purified from AME reduced cell spreading and increased cell rounding as soon as 2 h upon introduction to the medium. The MTT assay showed that HC•HA complex purified from AME significantly decreased the cell viability more so than HMW HA or AME alone (P=0.002 and 0.02, respectively) (FIG. 7).

To further confirm that such an inhibitory activity on macrophage viability resided in HC•HA complex, we compared HC•HA complex purified from AME (termed native HC•HA or nHC•HA) to that in vitro reconstituted (rcHC•HA; see above) using the macrophage MTT assay.

Figure 6:
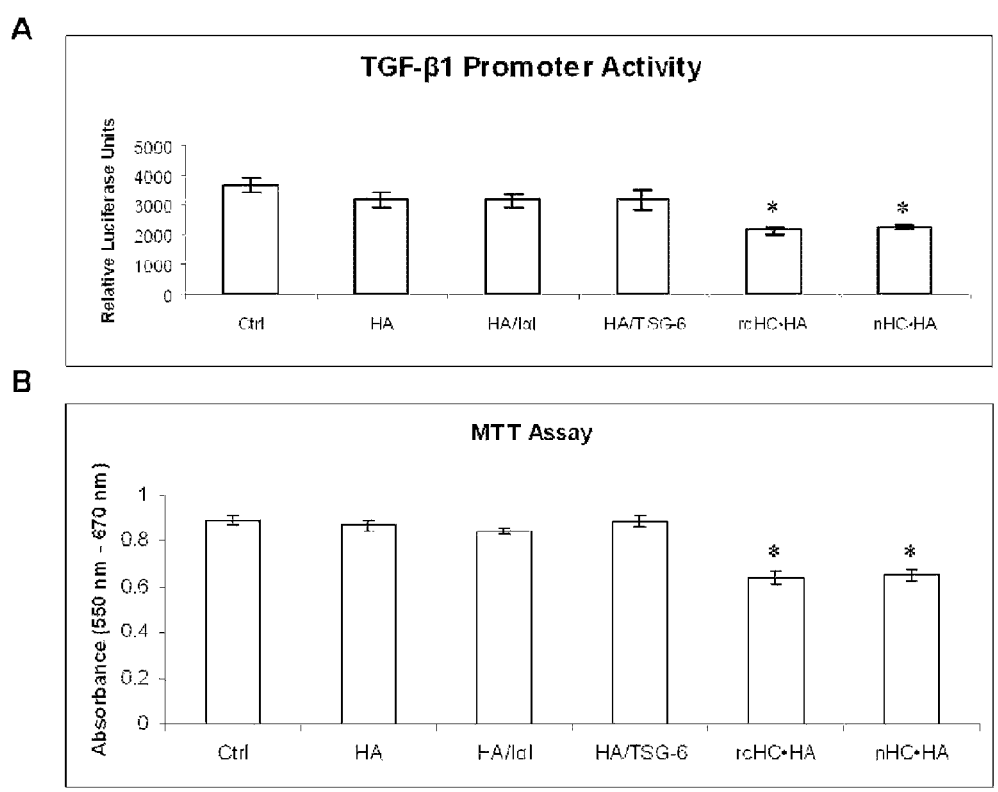
FIG. 6. As compared to PBS as the control (Ctrl), rcHC•HA complex or nHC•HA significantly suppressed TGF-β1 promoter activity, i.e. as measured by the TGF-β1 promoter assay (A, p=0.004 and 0.005, respectively), and promoted macrophage death as measured by the MTT assay (B, p=0.0003 and 0.0007, respectively). In contrast, HMW HA alone (HA) or with additional IαI (HA+IαI) or TSG-6 (HA+TSG-6) did not show any effect (all p>0.05).

Compared to the control cultured on the HABP-coated dish (Ctrl), addition of HMW HA alone (HA) and addition of HMW HA with either 40 μg/ml I_I (HA/IαI) or 6 μg/ml TSG-6 (HA/TSG-6) did not cause any significant difference in macrophage viability (P=0.30, 0.19, and 0.08, respectively) (FIG. 6A).

In contrast, both rcHC•HA and nHC•HA significantly reduced the macrophage viability (P=0.0003 and 0.007, respectively, FIG. 6A), while rcHC•HA and nHC•HA exhibited a similar inhibitory activity (P=0.64, FIG. 6A).

To determine whether nHC•HA and rcHC•HA exerted a similar anti-scarring action, we seeded $3 \times 10^4$/ml of human corneal fibroblasts, which had been transfected with adenovirus containing either TGF-β1 promoter-luciferase or CMV-β-gal for 48 h before being subjected to the TGF-β1 promoter activity assay. Compared to the control (Ctrl), the TGF-β1 promoter activity was not significantly suppressed by HA, HA/IαI, or HA/TSG-6 (P=0.07, 0.06 and 0.10, respectively, FIG. 6B). In contrast, both rcHC•HA and nHC•HA showed significant suppression (P=0.004 and 0.005, respectively, FIG. 6B).

Again, the extent of suppression of TGF-β1 promoter activity exerted by nHC•HA was not significantly different from rcHC•HA (P=0.20). The same result was obtained by adding these components as a solution in the well (without being bound to HABP-crosslinked dish).

Example 7

HA in AM is Covalently Linked with HCs of IαI

To investigate whether IαI is covalently linked with HMW HA in AM extracts, we used either HAase to digest HA into small fragments (that would run on SDS-PAGE) or weak NaOH to hydrolyze any ester bonds between HCs and HA. HMW HA in these extracts was completely digested by 20 units/ml HAase at 37° C. for 2 h, but was not hydrolyzed by 0.2 N NaOH at 25° C. for 4 h. However, we found the amount of total proteins visualized by Coomassie blue staining in Extracts A, B, and C after 0.2 N NaOH treatment appeared to be less than those without such treatment.

To optimize NaOH treatment so as not to cause protein hydrolysis, we subjected Extract A to a range of NaOH concentrations at 25° C. for 1 h. Similar to what had been reported, purified IαI (FIG. 1A, lane 2) yielded a major band at ~250-kDa when analyzed by Western blotting, representing the intact IαI. Other bands with smaller MWs were also seen, which are presumably degradation products of IαI.

Untreated Extract A contained a band corresponding to IαI, but also had a HMW band still remaining in the gel loading well and two other major bands of 75- and 120-kDa (FIG. 1A, lanes 3 and 4). The HMW band is likely to be IαI components covalently linked with HMW HA, where their size precludes them from entering the gel. The 75-kDa band is presumed to correspond to a free HC and 120-kDa band is likely to be one HC covalently coupled to either the bikunin or TSG-6.

Treatment with 0.02 N NaOH caused a large reduction of IAI-immunoreactive bands, with the exception of the 120-kDa species, and dramatically increased the intensity of 75-kDa band and the emergence of an 80-kDa band, where the 75- and 80-kDa species are likely to correspond to HC1 and HC2, respectively.

Treatment with 0.05-0.2 N NaOH led to complete removal of all bands except for the 75- and 80-kDa bands, where the highest concentrations of NaOH had a somewhat lower intensity of these bands, presumably due to protein hydrolysis. Therefore, in the subsequent experiments 0.05 N NaOH was chosen to treat AM extracts and the results were compared with those digested with HAase.

Coomassie blue staining showed that the sample loading of Extracts A, B and C was similar for non-treated (None), HAase digested (HAase), and NaOH treated (NaOH) samples. Therefore, the same samples were then used for the Western blot analysis with anti-IαI antibody. As shown in FIG. 1B, non-treated Extract C (lane 5) had similar band profiles to that of Extract A described above (FIG. 1A, lane 3 and FIG. 1B, lane 3), whereas no IAI was detected in Extract B (lane 4). HAase digestion (lanes 6-8) completely removed the HMW band (retained in the well) in Extracts A and C, suggesting that this band is a HMW IαI-HA complex. For Extracts A and C, the 75-kDa band was increased after HAase digestion, where it also became visible in Extract B. These results clearly demonstrated that HCs and HA were linked and present in both water soluble (Extracts A, B and P) and water insoluble (Extract C) extracts.

Noticeably, the 250- and 120-kDa bands became much sharper and more intense following HAase digestion (FIG. 1B, lanes 6 and 8) indicating that some of these species may be released from HA.

Because both 250- and 120-kDa bands were completely eliminated by 0.05 N NaOH (FIG. 1A), resulting in the most increase of the 75-kDa band (the 80-kDa band was difficult to see at most time points) (FIG. 1B, lanes 9-11), this indicated that the 250- and 120-kDa bands are complexes of HCs and other components linked by ester bonds. These results are therefore consistent with the conclusion that the 250- and 120-kDa species correspond to intact IAI and a HC-containing complex (e.g., HC•bikunin or TSG-6•HC), respectively.

Example 8

Suppression of TGF-β by AM Isotonic Extract

Figure 3:
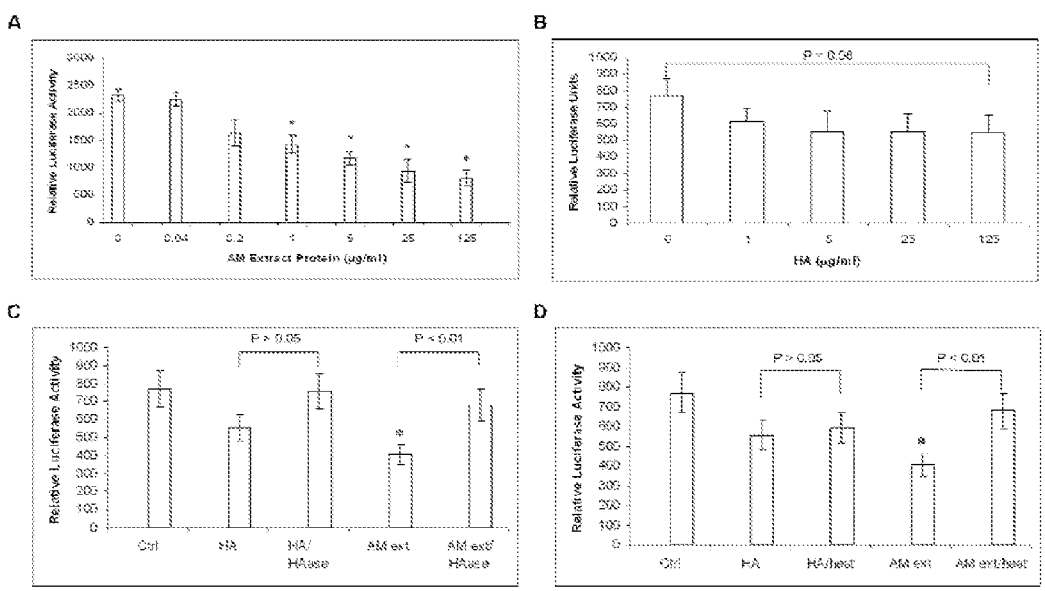
FIG. 3. A dose-dependent relationship was noted in the suppression of the TGF-β1 promoter activity by a series of concentrations of Extract P (A). In contrast, there was not such a relationship by a series of concentrations of HMW HA (B). The suppressive effect of the TGF-β1 promoter activity was lost when Extract P (125 μg/ml proteins), by not HMW HA (125 μg/ml) was digested with hyaluronidase (C) or heat-treated (95° C. for 10 min) (D). In A, B, C, and D, an astark (*) indicated p<0.05 (n=4).

To test whether Extract P suppressed TGF-β transcription, we used a luciferase based TGF-β1 promoter assay. The suppression of TGF-β1 promoter activity in human corneal fibroblasts was dose-dependent over the range of protein concentrations from 0.2 to 125 μg/ml of Extract P (FIG. 3A). As low as 1 μg/ml proteins significantly suppressed TGF-β1 promoter activation and there was a greater than 50% suppression when 125 μg/ml proteins (containing ~5 μg/ml HA) was added (p=0.008). In contrast, 1 μg/ml of the control HMW HA (medical grade) did not significantly suppress TGF-β1 promoter activation (P=0.20, FIG. 3B). No significant suppression of the promoter activity was achieved by 5, 25, and 125 μg/ml of HMW HA (P=0.10, 0.09, and 0.06, respectively, FIG. 3B).

To further test whether this activity was related to HA alone or HA-protein complex, both HMW HA and Extract P were digested with HAase or heated at 95° C. for 10 min before testing. The results showed that both treatments abolished the significant suppressive effect of Extract P (P=0.06 and 0.12 for HAase and heat treatment, respectively, FIGS. 3C and 3D). In contrast, they did not cause significant change in HMW HA-treated group (P=0.31 and 0.70, for HAase and heat treatment, respectively, FIGS. 5C and 5D). These data indicated both HA and proteins in Extract P were necessary for suppressing the TGF-B1 promoter activity.

Example 9

Characterization and Validation of Anti-Angiogenic Actions of an HC•HA Complex

AME is prepared as described above. HC•HA complex is purified from the AME using two rounds of ultracentrifugation in CsCl and 4M guanidine HCl. AME and HC•HA Complex are serially diluted.

Experiments 1A

The relative anti-angiogenic potency of AME and HC•HA is compared based on the same μg/ml HA in the following 4 in vitro assays using HUVEC cultured in the endothelial cell growth medium supplemented by 2% FBS, 0.1 ng/ml EGF, 1 μg/ml hydrocortisone, and 1 ng/mL bFGF with or without 1 to 100 μg/ml VEGF: (1) MMP Activity based on zymogen assay using MMP substrates such as collagen, fibringogen, or gelatin, (2) Proliferation based on morphology, the MTT assay, BrdU labeling and Live & Dead assay; (3) Migration based on chemotaxis, and (4) Tube Formation of HUVEC in Matrigel.

Experiment 1B

Afterwards, in Exp. #1B, the anti-angiogenic action of the purified HC•HA complex is examined in the following in vivo assays: (1) Chick chorioallantoic membrane (CAM) assay, (2) in vivo Matrigel assay in right lower abdomen of female mice, and (3) Corneal angiogenesis assay. For these three in vivo assays, the angiogenesis will be induced by impregnating bFGF or VEGF or both in either Matrigel or ELVAX (ethylene vinyl copolymer) with or without an HC•HA complex at a concentration determined in Exp. #1A.

For both Exp. #1A and Exp. #1B, the anti-angiogenic action of an HC•HA complex will be compared to that of the control of medical grade HMW HA (Healon™, Advanced Medical Optics, CA) at the same μg/ml HA, and that of the PBS as the negative control. A minimum of sample size of 5 will be used for statistical analyses.

Example 10

Exploration of How an HC•HA Complex Disrupts Signaling Mediated by HA Receptors and VEGFR For both experiments below, the anti-angiogenic action of an HC•HA complex will be compared to that of HMW HA.

Experiment #2A

HUVEC cells are pre-incubated with antibodies to CD44 (Cat#16-0441, eBioscience, San Diego, Calif.), RHAMM, HARE, or TLR while using their respective isotype antibodies as the control. HUVEC morphology, viability, proliferation and death will similarly assessed as described in Exp. #1B and compared among PBS control, HMW HA, and an HC•HA complex.

Experiment #2B

For a time frame from 15 min to 2 h with or without addition of VEGF, of which the optimal concentration has been determined in Exp. #1B, HUVEC lysates are collected and subjected to western blot analyses using antibodies specific to phosphorylated or total ERK, PI3K and Akt using histone 3 as the loading control.

Example 11

Validation of the Potency of Purified HC•HA Complex in Exerting in Vitro Anti-Inflammatory and Anti-Scarring Actions The potency of HC•HA complex in exerting anti-inflammatory and anti-scarring actions is demonstrated by macrophage MTT assay with or without activation by 200 U/ml IFN-γ in DMEM with ITS as well as by TGF-β1 promoter assay using human corneal fibroblasts cultured in DMEM/FBS, respectively. These results are compared to the positive controls including cryopreserved AM and AME, and the negative controls including plastic and HMW HA alone.

Furthermore, the relative potency between HC•HA complex and AME based on the same μg/ml of HA is determined by submitting their serial dilutions to these two assays using HMW HA alone as the negative control. The most appropriate concentration of HC•HA complex based on μg/ml of HA is then used to validate its anti-inflammatory potency by correlating its MTT assay with other assays of macrophage death/apoptosis such as LIVE/DEAD assay (Molecular Probes), Hoechst-33342 nuclear staining, and Cell Death Detection ELISAPLUS kit (Roche). Furthermore, these results are correlated with macrophage activation judged by membrane expression of MHCII, CD80 and CD86, with western blot analysis of Cox-2 expression (FIG. 12), and with the PGE2/PGD2 ratio (FIG. 13), and levels of anti-inflammatory (IL-10) and proinflammatory (IL-1, IL-6, and TNF-α cytokines by ELISA assays. Similarly, the anti-scarring potency judged by suppression of TGF-β1 promoter activity is correlated with phenotypic change of human keratocytes or human amniotic stromal mesenchymal cells into fibroblasts and myofibroblasts as judged by expression of keratocan, Factin, ED-A fibronectin, S-100A4, and α-SMA using immunostaining and Western blot analysis, and by monitoring Smad-mediated signaling using immunocytolocalization of Smads 2, 3 and 4.

Example 12

Comparison of HC•HA Complex Extracted from Amniotic Membrane and Chorionic Membrane HC•HA complex was extracted from chorionic membrane using the same protocols used for extracting HC•HA complex from amniotic membrane.

TABLE 2

Extract Yield, Protein & HA Content for 3 Donors with Entire Chorion except for Donor 1, from which a part was included. Data regarding HA for Donor 2 was excluded due to loss of sample resulted from a broken dialysis tube. The volume of extract sampled for each Donor for purification is 10.97 ml).

|  | Donor 1 | Donor 2 | Donor 3 | Average |
|---|---|---|---|---|
| Extract Yield | | | | |
| Wet Weight (g) | 10.0 | 17.7 | 29.1 | 59.0 | 38 ± 18 |
| Powder Weight (g) | 5.5 | 11.4 | 19.2 | 54.6 | 30 ± 21 |
| Loss of Tissue (%) | 45 | 36 | 34 | 7 | 31 ± 16 |
| PBS (ml) | 11.1* | 11.4 | 19.2 | 54.6 | 36 ± 25*** |
| Extract ml | 12.0* | 12.5 | 24.0 | 63.0 | 44 ± 28*** |
| Protein & HA Before Purification | | | | |
| Protein conc. (µg/ml Extract) | 1884 | 1764 | 1828 | 1826 ± 60 |
| Total Protein (µg) | 23555** | 42343 | 115201 | 78772 ± 51519*** |
| HA conc. (µg/ml Extract) | 0.90 | 0.96 | 0.92 | 0.93 ± 0.03 |
| Total HA (µg) | 11.3** | 22.9 | 57.7 | 40.3 ± 24.6*** |
| HA:Protein Ratio | 1:2093 | 1:1868 | 1:1987 | 1:1982 ± 113 |
| After Purification | | | | |
| Protein Conc. (µg/ml Purified Extract) | 172 | 62 | 136 | 123 ± 56 |
| Total Protein (µg)**** | 825.4 | 297.6 | 650.7 | 591 ± 269 |
| HA (µg/ml Purifed Extract) | 0.59 | — | 0.84 | 0.72 ± 0.02 |
| Total HA (µg)**** | 2.85 | — | 4.02 | 3.43 ± 0.83 |
| HA:Protein Ratio | 1:292 | — | 1:162 | 1:227 ± 93 |
| Protein Purity Factor (µg/ml Extract)/(µg/ml Purified Extract) | 11 | 28 | 13 | 17 ± 8 |
| HA Yield (%) (Total HA after purification/Total HA before purification) | 25.2 | — | 7.0 | 16.1 ± 12.9 |
| Total HA yield/ml CHE (µg/ml CHE) | 0.26 | — | 0.37 | 0.31 ± 0.08 |
| Total HA yield/chorion (µg/total extract (ml) from whole chorion) | 6.36 | — | 23.09 | 14.7 ± 11.8 |

*PBS was added to Extract at ratio of 1:2 (Extract:PBS). This portion of extract was excluded from the rest of the measurements.
**Calculated based on an extract portion of 12.5 ml
***Average based on Donor 2 & Donor 3 only
****Based on final volume of Purified Extract which is 4.8 ml per Donor There was significant loss of tissue during pulverizing (31±16%) and further loss of tissue during homogenization to reduce the wet tissue into powder and extract form subsequently. An alternative is to use a blender and homogenizer for large scale preparation of AM & Jelly lysate and Placenta extract.

TABLE 3

Average protein & HA Concentration and Ratio of CHE in comparison to AME before and after purification.

| | Extract | | | Purified Extract | | | HA yield | HA yield (µg/Total |
|---|---|---|---|---|---|---|---|---|
| | Protein (µg/ml) | HA (µg/ml) | HA:Protein Ratio | Protein (µg/ml) | HA (µg/ml) | HA:Protein Ratio | (µg/ml Extract) | Extract (ml) from whole AM/CH |
| AME | 214 ± 36 | 28.6 ± 5.3 | 1:7.5 | undetectable | 41.2 ± 1.8 | — | 72.1 | ~2163* |
| CHE | 1826 ± 60 | 0.93 ± 0.03 | 1:1963 | 123 ± 56 | 0.72 ± 0.02 | 1:227 ± 93 | 0.31 ± 0.08 | 14.73 ± 11.83 |

(1) *Calculated based on extract volume of AM ~30 ml (The Yield of HC•HA Purified from One AM-Hua He)

From Table 3, it is noted that the protein content in CHE is significantly to AME in both the extract and the purified extract. In contrast, the HC•HA content (measured by HA content) is significantly lower in CHE compared to AME before and after purification. The low percent yield of HA (6-25%) as seen in Table 1 is due to the high protein content after ultracentrifugation resulting in a small final pool fraction volume (4.8 ml per donor). The high protein concentration in CHE after the 2 rounds of ultracentrifugation may be due to the high protein content before purification relative to AME (~8.5 times fold) and may need a $3^{rd}$ round of ultracentrifugation to increase purity. Another reason for the proteins which remain present even after two rounds of ultracentrifugation with CsCl and guanidine is that there may be a strong binding between the proteins and the HC•HA complexes. These proteins may potentially have significant roles in promoting the formation and/or regulating the function of HC•HA complex. We are currently in the process of identifying and characterizing these proteins Example 13

BrdU ELISA-Dosage Curve for HC•HA(AME) and HC•HA(CHE) with Fibronectin Coating and VEGF 96-well plates (n=3) are coated with fibronectin. HUVEC are then seeded at 4000 cells/well HC•HA in the precoated wells for 48 hours (see table below). Two groups (n=3) with 10 ng/ml VEGF (Old VEGF-(receive date) or New VEGF (receive date: Mar. 10, 2010)) added simultaneously during seeding are included. BrdU label are added for last 6 hours of culturing period. BrdU ELISA performed as described in H-095.

TABLE 4

HA concentrations for HC•HA (AME) and HC•HA (CHE) to establish a dosage curve.
HA Concentration (µg/ml)

| | | | | | | | | | | |
|---|---|---|---|---|---|---|---|---|---|---|
| HC•HA (AME) | 25 | 12.5 | 5 | 1 | 0.5 | 0.25 | 0.05 | 0.025 | 0.01 | 0.005 |
| HC•HA (CHE) | — | — | — | 1 | 0.5 | 0.25 | 0.05 | 0.025 | 0.01 | 0.005 |
| Control (Medium) | | | | | | 0 | | | | |
| Old VEGF | | | | | | 0 | | | | |
| New VEGF | | | | | | 0 | | | | |

At 48 hours, control cells are mostly spindle shaped and the cell density has significantly increased since 24 hours. No difference is observed between the New VEGF group and control group. The cell density in the Old VEGF group appears to be noticeably less than control. In the HC•HA (AME) and HC•HA (CHE) groups, the cell density is significantly less in the 25 µg/ml and 1 µg/ml samples respectively and increases with decreasing HC•HA concentration. No difference can be seen between cells in control group and cells in groups with HC•HA concentration below 1 µg/ml for HC•HA (AME) and 0.05 µg/ml for HC•HA (CHE). Compared to 24 hours, the cells treated with HC•HA (AME and CHE) have become flatter.

CONCLUSIONS

BrdU ELISA is more sensitive and better to illustrate the dose-dependent changes than morphological changes.

Dose-dependent inhibition of proliferation by HC•HA (CHE) and HC•HA (AME) follows a logarithmic curve.

Lowest effective dose of HC•HA (CHE) as measured by BrdU ELISA is between 0.25 and 1 µg/ml, while that of HC•HA (AME) is between 1 and 5 µg/ml.

HC•HA (CHE) is 25 fold more potent than HC•HA (AME) according to IC50 (3.0 vs 0.12) based on HA concentration.

What is claimed is:

1. A method of producing a reconstituted HC•HA (rcHC•HA) complex, comprising
    (a) providing HA Binding Protein (HABP) crosslinked to a stationary support;
    (b) contacting the HABP crosslinked to the stationary support with
        (i) hyaluronan (HA);
        (ii) HC1 and HC2 of IαI; and
        (iii) TSG-6; and
    (c) incubating for a period of time sufficient to produce rcHC•HA complex.

2. The method of claim 1, wherein HC1 and HC2 of IαI are isolated from serum.

3. The method of claim 1, wherein at least one of HA, HC1, HC2, TSG-6, TSG-6-like protein is generated by a plurality of cells in the reaction mixture.

4. The method of claim 1, further comprising isolating and purifying the rcHC•HA complex.

5. The method of claim 4, wherein the rcHC•HA complex is isolated by centrifugation, filtration, or a combination thereof.

6. The method of claim 4, wherein the rcHC•HA complex is purified by chromatography, gel filtration, centrifugation, differential solubility, ethanol precipitation, or a combination thereof.

7. The method of claim 6, wherein the chromatography is affinity chromatography.

* * * * *